United States Patent [19]

Wong et al.

[11] Patent Number: 5,082,668

[45] Date of Patent: Jan. 21, 1992

[54] CONTROLLED-RELEASE SYSTEM WITH CONSTANT PUSHING SOURCE

[75] Inventors: Patrick S. L. Wong, Palo Alto; Brian L. Barclay, Sunnyvale; Joseph C. Deters; Felix Theeuwes, both of Los Altos, all of Calif.

[73] Assignee: Alza Corporation, Palo Alto, Calif.

[21] Appl. No.: 595,140

[22] Filed: Oct. 9, 1990

Related U.S. Application Data

[63] Continuation-in-part of Ser. No. 212,552, Jun. 28, 1988, which is a continuation-in-part of Ser. No. 912,712, Sep. 29, 1986, Pat. No. 4,783,337, which is a continuation-in-part of Ser. No. 685,687, Dec. 24, 1984, abandoned, which is a continuation-in-part of Ser. No. 493,760, May 11, 1983, abandoned.

[51] Int. Cl.$^5$ ............................................. A61K 9/22
[52] U.S. Cl. ................................... 424/473; 424/465
[58] Field of Search .......................................... 424/473

[56] References Cited

U.S. PATENT DOCUMENTS

| | | | |
|---|---|---|---|
| 4,008,719 | 2/1977 | Theeuwes et al. | 128/260 |
| 4,014,334 | 3/1977 | Theeuwes et al. | 128/260 |
| 4,063,064 | 12/1977 | Saunders et al. | 219/121 |
| 4,077,407 | 3/1978 | Theeuwes et al. | 128/260 |
| 4,093,708 | 6/1978 | Zaffaroni et al. | 424/15 |
| 4,111,202 | 9/1978 | Theeuwes | 128/260 |
| 4,160,020 | 7/1979 | Ayer et al. | 424/15 |
| 4,186,184 | 1/1980 | Zaffaroni | 424/14 |
| 4,200,098 | 4/1980 | Ayer et al. | 128/260 |
| 4,207,893 | 6/1980 | Michaels | 128/260 |
| 4,210,139 | 7/1980 | Higuchi | 128/260 |
| 4,285,987 | 8/1981 | Ayer et al. | 427/3 |
| 4,298,003 | 11/1981 | Theeuwes et al. | 128/260 |
| 4,320,759 | 3/1982 | Theeuwes | 128/260 |
| 4,327,725 | 5/1982 | Cortese et al. | 128/260 |
| 4,350,271 | 9/1982 | Eckenhoff | 222/386.5 |
| 4,455,143 | 6/1984 | Theeuwes et al. | 604/890 |
| 4,608,048 | 8/1986 | Cortese et al. | 604/890 |
| 4,610,686 | 9/1986 | Ayer et al. | 604/890 |
| 4,612,008 | 9/1986 | Wong et al. | 604/892 |
| 4,643,731 | 2/1987 | Eckenhoff | 604/892 |

Primary Examiner—Thurman K. Page
Attorney, Agent, or Firm—Paul L. Sabatine; Edward L. Mandell; Jacqueline S. Larson

[57] ABSTRACT

A device is disclosed comprising a wall that surrounds a compartment. The compartment comprises a beneficial agent composition and a push composition. A passageway in the wall connects the compartment with the exterior of the device for delivering the beneficial agent at a rate governed, in combination, by the wall, the beneficial agent composition and the push composition through the passageway of the device over time.

3 Claims, 7 Drawing Sheets

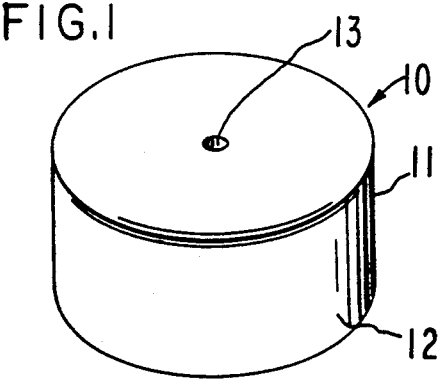
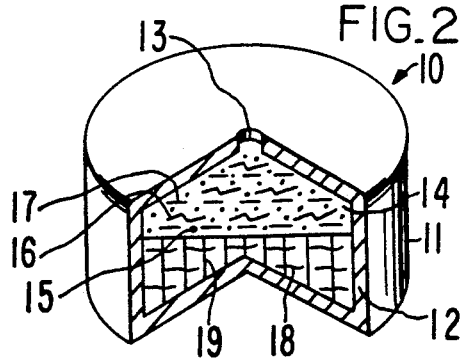
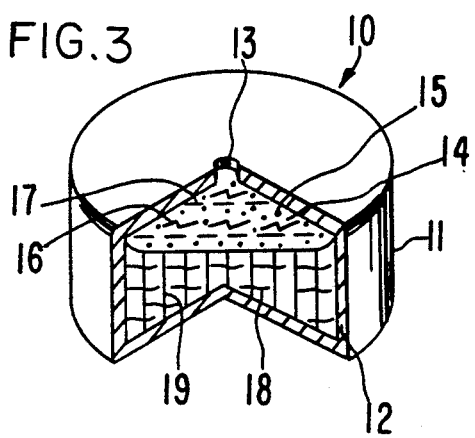
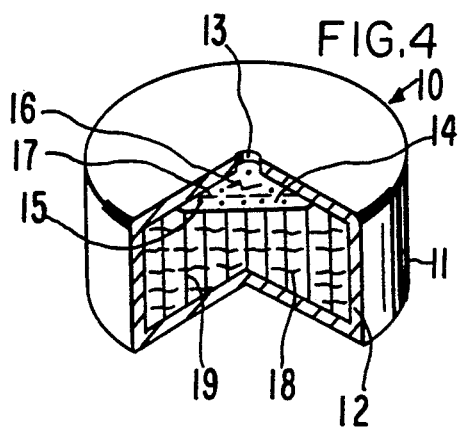
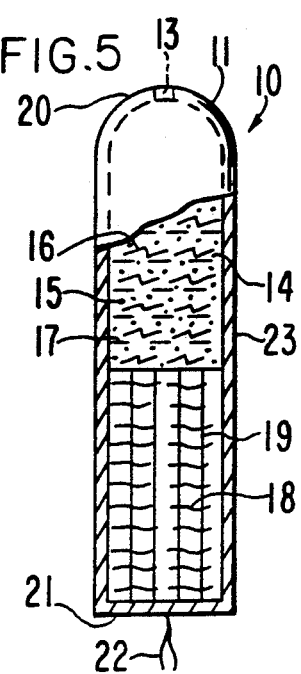
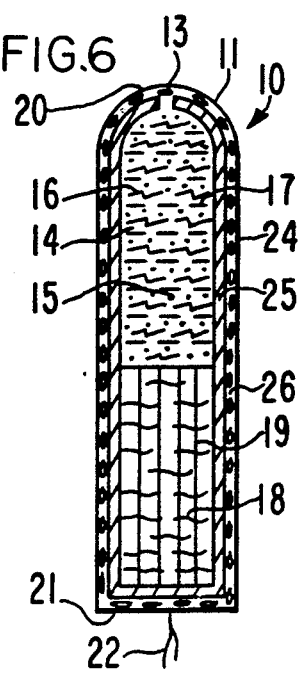
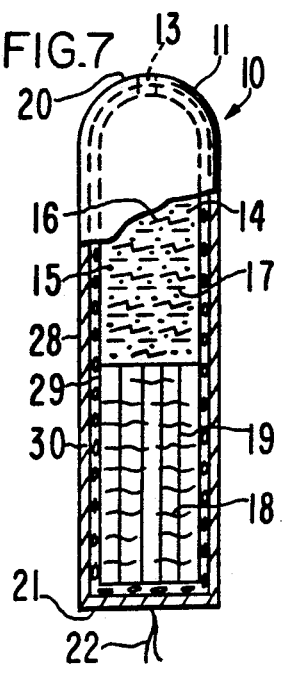

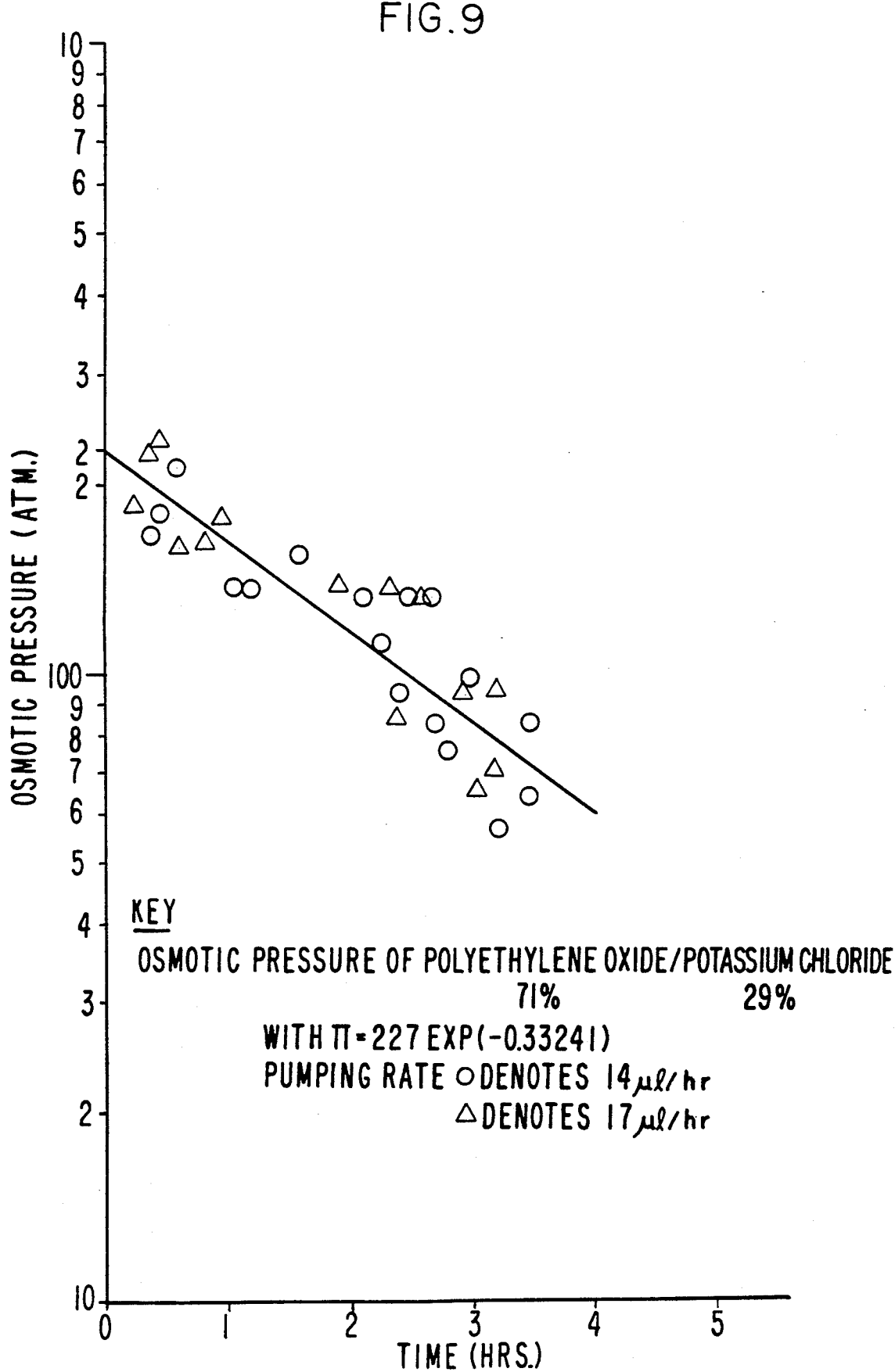

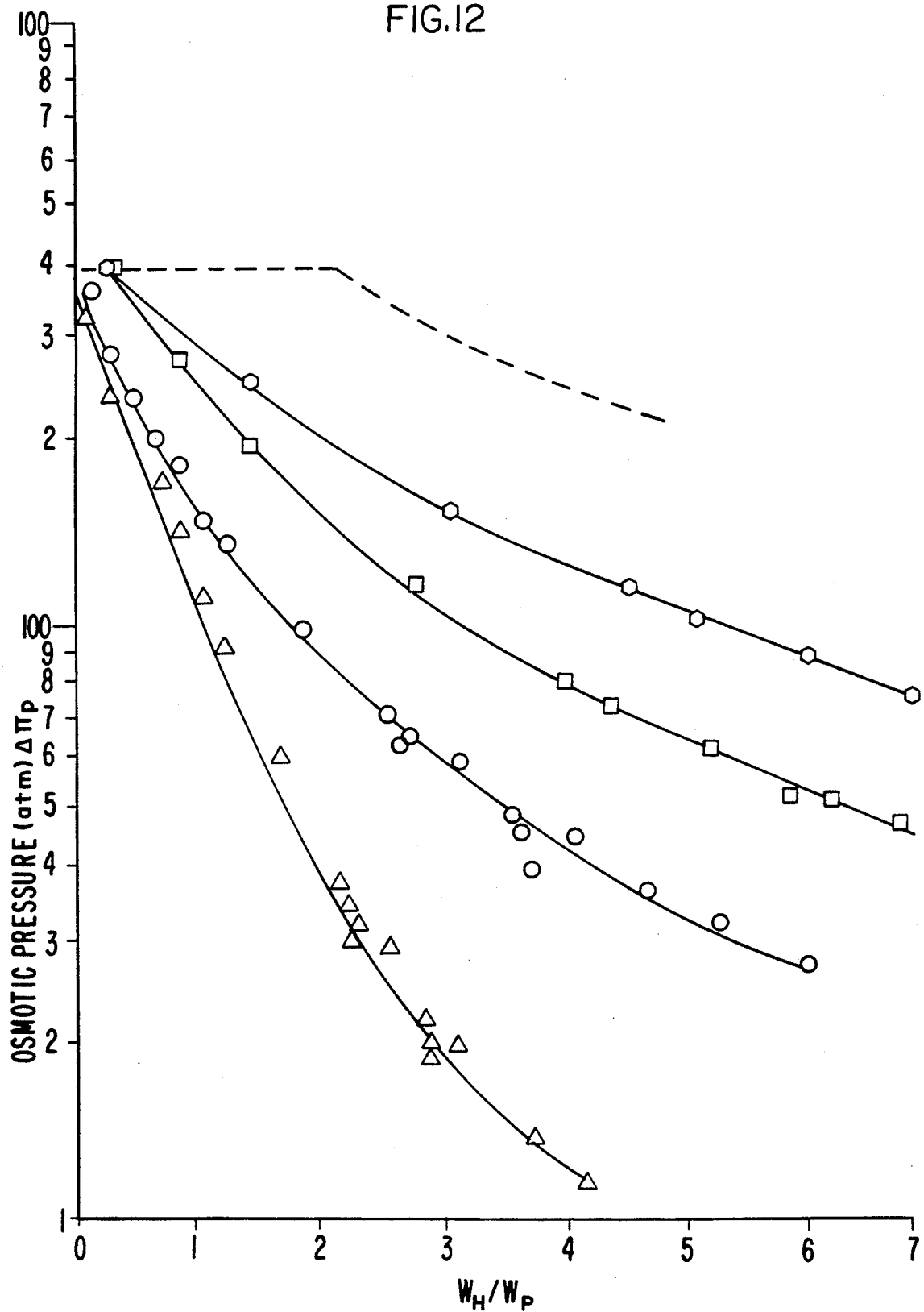

CONTROLLED-RELEASE SYSTEM WITH CONSTANT PUSHING SOURCE

This patent application is a continuation-in-part of U.S. Pat. Appln. Ser. No. 07/212,552, filed on June 28, 1988 which patent application is a continuation-in-part of U.S. Pat. Appln. Ser. No. 06/912,712, filed on Sept. 29, 1986, now U.S. Pat. No. 4,783,337 issued on Nov. 8, 1988, which Appln. Ser. No. 06/912,712 is a continuation-in-part of U.S. Pat. Appln. Ser. No. 06/685,687 filed on Dec. 24, 1984 (now abandoned), which Appln. Ser. No. 06/685,687 is a continuation-in-part of U.S. Pat. Appln. Ser. No. 06/493,760 filed May 11, 1983 (now abandoned), which applications are incorporated herein by reference and benefits are claimed of their filing dates. These patent applications are assigned to the ALZA Corp., of Palo Alto, Calif.

This invention pertains to both a novel and unique delivery system. More particularly, the invention relates to a delivery device comprising a wall that surrounds a compartment comprising: (1) a first composition comprising a beneficial agent, an osmopolymer and optionally an osmagent, said first composition in arrangement with (2) a second composition comprising a constant pushing means for pushing the first composition from the device. The device comprises at least one passageway through the wall that connects the exterior of the device with the compartment for delivering the first composition comprising the beneficial agent from the device. The device in one presently preferred embodiment is useful for delivering (3) beneficial agents that because of their solubilities are difficult to deliver in a known amount at a controlled rate from a delivery device, and for delivering (4) beneficial agents that are therapeutically very active and are dispensed in small amounts, that is in minidoses, at a controlled rate from the dispensing system.

BACKGROUND OF THE INVENTION

Since the beginning of antiquity, both pharmacy and medicine have sought a delivery system for administering a beneficial drug. The first written reference to a delivery system is in the Eber Papyrus, written about 1552 B.C. The Eber Papyrus mentions delivery systems such as anal suppositories, vaginal pessaries, ointments, oral pill formulations, and other delivery systems. About 2500 years passed without any advance in dosage form development, when the Arab physician Rhazes, 865–925 A.D., invented the coated pill. About a century later the Persian Avicenna, 980–1037 A.D., coated pills with gold or silver for increasing patient acceptability and for enhancing the effectiveness of the drug. Also around this time, the first tablet was described in Arabian manuscripts written by al-Zahrawi, 936–1009 A.D. The manuscripts described a tablet formed from the hollow impressions in two facing tablet molds. Pharmacy and medicine waited about 800 years for the next innovation in delivery systems when, in 1883, Mothes invented the capsule for administering drug. The next quantum leap in dosage forms came in 1972 with the invention of the osmotic delivery system by inventors Theeuwes and Higuchi as disclosed in U.S. Pat. Nos. 3,845,770 and 3,916,889.

The osmotic systems disclosed in U.S. Pat. Nos. 3,845,770 and 3,916,889 comprise in at least part a semipermeable wall that surrounds a compartment containing a beneficial agent. The semipermeable wall is permeable to the passage of an external fluid, and it is substantially impermeable to the passage of a beneficial agent. There is at least one passageway through the wall for delivering the beneficial agent from the osmotic system. These systems release a beneficial agent by fluid being imbibed through the semipermeable wall into the compartment at a rate determined by the thickness and permeability of the semipermeable wall and the osmotic pressure gradient across the semipermeable wall to produce an aqueous solution containing a beneficial agent that is dispensed through a passageway from the system. These systems are extraordinarily effective for delivering a beneficial agent that is soluble in the fluid and exhibits an osmotic pressure gradient across the semipermeable wall against the external fluid.

A pioneer advancement in osmotic delivery systems, manufactured in the form of an osmotic device, was presented to the dispensing arts by inventor Felix Theeuwes in U.S. Pat. No. 4,111,202. In this patent, the delivery kinetics of the osmotic device is enhanced for delivering beneficial agents, including drugs, that are insoluble to very soluble in the fluid, by manufacturing the osmotic device with a beneficial agent compartment and an osmagent compartment separated by an internal film. The internal film is movable from a rested to an expanded state. The osmotic device delivers the beneficial agent by fluid being imbibed through the semipermeable wall into the osmagent compartment producing a solution that causes the compartment to increase in volume and act as a driving force that is applied against the film. This force urges the film to expand in the device against the beneficial agent compartment and, correspondingly, diminish the volume of the beneficial agent compartment, whereby beneficial agent is dispensed through the passageway from the osmotic device. While this device operates successfully for its intended use, and while it can deliver numerous useful agents of varying solubilities, its use can be limited because of the manufacturing steps and costs needed for fabricating and placing the movable film in the compartment of the osmotic device.

In the U.S. Pat. No. 4,327,725 patentees Richard Cortese and Felix Theeuwes provided an osmotic dispensing device for delivering beneficial agents that, because of their solubilities in aqueous and biological fluids, are difficult to deliver in meaningful amounts at controlled rates over time. The osmotic devices of this patent comprise a semipermeable wall surrounding a compartment containing a beneficial agent that is insoluble to very soluble in aqueous and biological fluids, and an expandable hydrogel. In operation the hydrogel expands in the presence of external fluid that is imbibed into the device thereby dispensing the beneficial agent through the passageway from the device. This device operates successfully for its intended use, and it delivers many difficult to deliver beneficial agents for their intended purpose.

Now it has been observed that the value of the prior art system described immediately above can be enhanced unexpectedly by the present invention providing an unobvious composition comprising the beneficial agent and a pharmaceutically acceptable carrier gel, which composition cooperates with a separate expanding hydrogel for pushing the beneficial agent from the device, thereby leading to improved administration and to improved therapy. It will be appreciated by those versed in the art, that if such an osmotic device can be provided that exhibits a high level of delivery activity, such an osmotic device would have a positive value and represent an advancement in the dispensing art. Likewise, it will be immediately appreciated by those versed in the dispensing art that if an osmotic device is made available possessing dual thermodynamic osmotic activity for delivering increased amounts of a beneficial agent accompanied by a pharmaceutically acceptable carrier at a controlled rate, said osmotic device would find practical application in the fields of pharmacy and medicine.

OBJECT OF THE INVENTION

Accordingly, in view of the above presentation, it is an immediate object of this invention to provide a delivery system that can be manufactured by standard manufacturing techniques into osmotic devices of various sizes, shapes and forms that represent a further improvement and advancement in the dispensing art.

Another object of the invention is to provide a delivery system manufactured in the form of an osmotic device for delivering in vivo a beneficial agent including drug that is difficult to delivery and now can be delivered by the device provided by this invention in therapeutically effective amounts over time.

Another object of the invention is to provide a delivery system possessing dual osmotic activity that operates as an integrated unit, which system comprises a compartment containing a first osmotic composition comprising a beneficial agent such as a drug, and an osmopolymer carrier for the agent or drug and optionally an osmagent, and a second osmotic composition comprising an osmopolymer, an optional osmagent and free of agent or drug, with the compositions acting in concert for delivering the drug through a passageway of controlled dimensions from the osmotic device.

Yet another object of the invention is to provide a delivery device having means for high loading of a water insoluble or a slightly water soluble beneficial agent such as a drug and means for delivering the beneficial agent in either instance at a controlled rate and continuously over time to a drug recipient.

Yet another object of the invention is to provide an osmotic device that can deliver a pH dependent beneficial agent by providing a neutral medium for delivering the beneficial agent in a finely dispersed form for increasing its surface area and for maximizing and dissolution rate of the beneficial agent.

Still yet another object of the invention is to provide an osmotic device for delivering a drug having a very low dissolution rate that is the rate limiting step for delivering the drug from the device, but now can be delivered by using an osmotic composition that functions in situ as a carrier that is delivered with the drug, thereby enhancing the drug's delivery from the osmotic device.

Another object of the invention is to provide an osmotic device comprising means for maintaining a high level of osmotic activity of a polymer which polymer is used for delivering a beneficial agent from the osmotic device.

Still a further object of the invention is to provide an osmotic, therapeutic device that can administer a complete pharmaceutical dosage regimen comprising poorly soluble to very soluble agents, at a controlled rate and continuously for a particular time period, the use of which requires intervention only for the initiation and possible termination of the regimen.

Still another object of this invention is to provide an osmotic device, which device can house a small amount of a therapeutic agent and dispense small doses, that is minidoses, of the therapeutic agent at a controlled rate to the gastrointestinal tract throughout the length of the gastrointestinal tract.

Still another object of the invention is to provide an improvement in an osmotic device manufactured with a compartment housing a first drug polymer means and a second drug free polymer means in spaced arrangement that simultaneously maintain their original identity and function as an integrated layered unit for delivering the beneficial drug accompanied by the first drug polymer means in paste or gel ribbon-like form from the osmotic device.

Still a further object of this invention is to provide a delivery device that possesses the ability to deliver drugs over a broad range of drug delivery rates, and can deliver the drugs according to a predetermined drug release rate pattern to a biological recipient over time.

A still further object of the invention is to provide a delivery system that avoids patient compliance problems and uses less drug, minimizes side effects and thereby provides efficiency in treatment for better health.

Other objects, features, aspects and advantages of the invention will be more apparent to those versed in the dispensing art from the following detailed specification taken in conjunction with the figures and the accompanying claims.

BRIEF DESCRIPTION OF THE DRAWINGS

In the drawings, which are not drawn to scale, but are set forth to illustrate various embodiments of the invention, the drawing figures are as follows:

FIG. 1 is an isometric view of a delivery device designed for orally administering a beneficial agent to the gastrointestinal tract;

FIG. 2 is an opened view of the device of FIG. 1 illustrating the structure of the device of FIG. 1;

FIG. 3 is an opened view of the device of FIG. 1 illustrating the device in operation and delivering a beneficial agent from the device;

FIG. 4 is an opened view of the device of FIG. 1 considered with FIG. 3 illustrating the device in operation and comprising more than one passageway for delivering a major amount of a beneficial agent from the device;

FIG. 5 shows a therapeutic device with its wall partially broken away, designed for delivering a beneficial agent into a body passageway, such as the ano-rectal and vaginal passageways;

FIG. 6 shows the device of FIG. 5 with a different wall structure;

FIG. 7 shows the device of FIG. 5 depicting a different wall structure than the wall structure depicted in FIG. 6;

FIG. 9 depicts the osmotic pressure of a polymer containing an osmagent that develops osmotic pressure at two different pumping rates;

FIG. 12 depicts the osmotic pressure curves for an osmagent and a number of osmopolymer/osmagent compositions;

In the drawings and the specification, like parts in related figures are identified by reference numerals. The terms appearing earlier in the specification and in the description of the drawings, as well as embodiments thereof, are further detailed elsewhere in the disclosure.

DETAILED DESCRIPTION OF THE DRAWINGS

Figure 8:
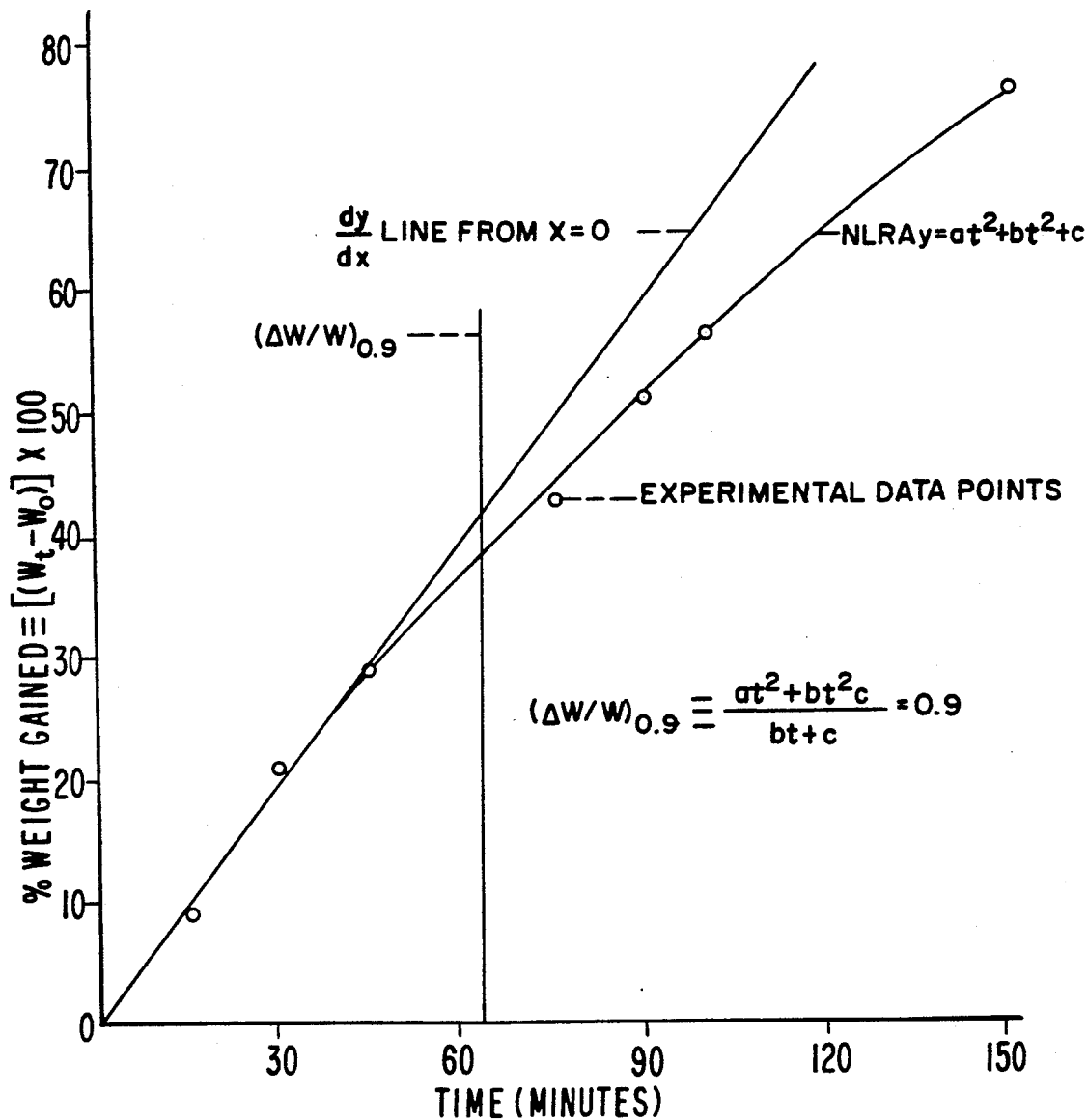
FIG. 8 represents the weight gain as a function of time for a polymer encapsulated in a semipermeable membrane when the encapsulated polymer is placed in water.

Turning now to the drawings in detail, which are examples of various devices provided by the invention, and which examples are not to be construed as limiting, one example of a device is seen in FIG. 1. In FIG. 1, device 10 is seen comprising a body member 11 having a wall 12 and at least one passageway 13 for releasing a beneficial agent from device 10 to a fluid environment of use. The phrase "fluid environment of use" as used for the purpose of this invention denotes the gastrointestinal tract, comprising the stomach and the intestine, and other fluid containing areas in an animal environment.

In FIG. 2, device 10 of FIG. 1 is seen in opened section. In FIG. 2, device 10 comprises a body 11, a wall 12 that surrounds and forms internal compartment 14, that communicates through a passageway 13 with the exterior of device 10. Wall 12 comprises totally a semipermeable composition or at least in part a semipermeable composition. When wall 12 comprises at least in part a semipermeable composition the remainder of the wall is comprised of a non-semipermeable composition. Compartment 14 contains a first composition comprising a beneficial agent 15, represented by dots, which agent 15 can be from insoluble to very soluble in fluid imbibed into compartment 14, an optional osmagent 16, represented by irregular lines, that is soluble in fluid imbibed into compartment 14 and exhibits an osmotic pressure gradient across semipermeable wall 12 against an external fluid and an osmopolymer 17, represented by horizontal dashes, that imbibes and/or absorbs fluid into compartment 14 and exhibits an osmotic pressure gradient across semipermeable wall 12 against an exterior fluid present in the environment of use. Wall 12 comprises a semipermeable composition that is substantially permeable to the passage of the exterior fluid, and it is substantially impermeable to the passage of agent 15, osmagent 16 and osmopolymer 17. Semipermeable wall 12 is non-toxic and it maintains its physical and chemical integrity during the delivery life of agent 15 from device 10.

Compartment 14 also houses a second composition that is distant from passageway 13 and in spaced relation with the first composition. The second composition contributes an expandable driving force that pushes and acts in cooperation with the first composition for delivering the maximum amount of beneficial agent 15 from device 10. The second composition comprises an optional osmagent 18, represented by wavy lines, that is soluble in fluid imbibed into compartment 14 and exhibits an osmotic pressure gradient across semipermeable wall 12 against an external fluid, blended with a presently preferred osmopolymer 19, represented by vertical lines, that imbibes fluid into compartment 14 and exhibits an osmotic pressure gradient across semipermeable wall 12 against external fluid. Osmopolymer 17 and osmopolymer 19 are hydrophilic water soluble or lightly cross-linked water soluble polymers, and they possess osmotic properties such as the ability to imbibe external fluid through the semipermeable wall, exhibit an osmotic pressure gradient across the semipermeable wall against the external fluid, and swell or expand in the presence of the fluid in the compartment. Osmopolymers 17 and 19 preferably are mixed with an optional osmagent 16 and an optional osmagent 18, respectively, for imbibing the optimal maximum volume of external fluid into compartment 14. This imbibed fluid is available to osmopolymers 17 and 19 to optimize the volumetric rate and for total expansion of osmopolymer 17 and 19. That is, osmopolymers 17 and 19 absorb fluid imbibed into compartment 14 by the osmotic imbibition action of osmopolymers 17 and 19 supplemented by the osmotic imbibition action of optional osmagents 16 and 18 for effecting the optimal maximum expansion of osmopolymers 17 and 19 from a rested to an enlarged, that is, an expanded state.

In operation, the delivery of beneficial agent 15 from osmotic device 10 is carried out, in one presently preferred embodiment, by (1) imbibition of fluid by the first composition to form a fluidic composition in situ and delivery of the suspension through the passageway; and concurrently by (2) imbibition of fluid by the second composition causing the second composition to swell and cooperate with the first composition for driving the agent formulation through at least one, or more than one, passageways. The agent formulation is preferably delivered as a ribbon, which is a viscous or paste-like strip. According to the operation described, the device may be considered as a cylinder, with the second composition expanding like the movement of a piston for aiding in delivering the beneficial agent composition from the device. For the purpose of the present analysis, the volume rate delivered by the device $F_t$ is composed of two sources: the water imbibition rate by the first composition F, and the water imbibition rate by the second composition Q wherein:

$$F_t = F + Q \tag{1}$$

Since the boundary between the first composition and the second composition hydrates very little during the functioning of the device, there is insignificant water migration between the compositions. Thus, the water imbibition rate of the second composition, Q, equals the expansion of its volume:

$$\frac{dv_p}{dt} = Q \tag{2}$$

The total delivery rate from the osmotic device is then, $$\frac{dm}{dt} = F_t \cdot C = (F + Q)C \tag{3}$$

wherein C is the concentration of beneficial agent in the delivered slurry or solution. Conservation of the osmotic device volume, V, and the surface area, A, gives equations (4) and (5):

$$V = V_d + V_p \quad (4)$$

$$A = A_d + A_p \quad (5)$$

wherein $V_d$ and $V_p$ equal the volumes of the first composition and the second composition, respectively; and wherein $A_d$ and $A_p$ equal the surface area in contact with the wall by the first composition and the second composition, respectively. In operation, both $V_p$ and $A_p$ increase with time, while $V_d$ and $A_d$ decrease with time as the device delivers beneficial agent.

The volume of the second composition that expands with time when fluid is imbibed into the compartment is given by equation (6):

$$V_p = f \frac{W_H}{W_p} \quad (6)$$

wherein $W_H$ is the weight of fluid imbibed by the second composition, $W_p$ is the weight of the second composition initially present in the device, $W_H/W_p$ is the ratio of fluid to initial solid of the second composition, and $$V_p = \left(1 + \frac{W_H}{W_p}\right)\frac{W_p}{\rho} \quad (7)$$

wherein $\rho$ is the density of the second composition corresponding to $W_H/W_p$. Thus, based on the geometry of a cylinder, where r is the radius of the cylinder, the area of imbibition is related to the volume of the swollen second composition as follows:

$$A_p = \pi r^2 + \frac{2}{r} \frac{W_p}{\rho} (1 + W_H/W_p) \quad (8)$$

The fluid imbibition rates into each composition are:

$$A_d = A - A_p \quad (9)$$

The fluid imbibiion rates into each composition are:

$$F = \left(\frac{k}{h}\right)(A_d \cdot \Delta \pi_d) \quad (10)$$

$$Q = \left(\frac{k}{h}\right)(A_p \cdot \Delta \pi_p) \quad (11)$$

wherein k equals the osmotic permeability of the wall, h equals the wall thickness, $\Delta \pi_d$ and $\Delta \pi_p$ are the osmotic gradients for the first composition and the second composition respectively. The total delivery rate, therefore, is equation (12):

$$\frac{dm}{dt} = \frac{k}{h} C \left\{ \left[ A - \pi r^2 - \frac{2}{r} \frac{W_p}{\rho}(1 + W_H/W_p) \right] \Delta \pi_d + \left[ \pi r^2 + \frac{2}{r} \frac{W_p}{\rho}(1 + W_H/W_p) \right] \Delta \pi_d \right\} \quad (12)$$

FIGS. 3 and 4 illustrate the osmotic device in operation as described for FIGS. 1 and 2. In FIGS. 3 and 4, for osmotic device 10, fluid is imbibed by the first composition at a rate determined by the permeability of the wall and the osmotic pressure gradient across the wall. The imbibed fluid continuously forms a composition comprising a beneficial agent and the gel, which composition is released by the combined operations of the first composition and the second composition device 10. These operations include the composition being osmotically delivered through the passageway due to the continuous formation of the composition, and by the swelling and increasing volume of the different second composition, is represented by the increase in height of the vertical lines in FIGS. 3 and 4. This latter swelling and increase in volume applies pressure against the first composition thereby aiding the first composition and simultaneously causing delivery of beneficial agent through the osmotic passageway to the exterior of the device. The device can comprise more than one passageway, a passageway made as a microporous insert, or drug releasing pores formed by leaching a leachable pore-former thereby providing pore-passageways for releasing drug to the exterior of the device. Thus, the osmotic device provided by this invention can be viewed as a single unit construction device comprising two compositions containing two polymeric structures acting in concert for effective drug administration to a patient.

The first composition and the second composition act together to substantially insure that delivery of beneficial agent from the compartment is controlled and constant over a prolonged period of time by two methods. First, the first composition imbibes external fluid across the wall, thereby forming a dispensalbe composition, which is substantially delivered at non-zero order rate, without the second composition present, since the driving force decays with time. Second, the second composition operating by imbibing external fluid across the wall continuously and, consequently, increases in volume as well as imbibition area, thereby exerting a force which can be constant, increasing or decreasing with time (depending on the osmotic formulation) against the first composition and diminishing the volume of beneficial agent first compositioon, thusly directing beneficial agent to the passageway at a controlled rate from the compartment. Additionally, as the first composition is squeezed out, that is, delivered from device 10, the osmotic composition closely contacts the internal wall and generates a constant osmotic pressure and, therefore, effects a constant delivery rate in conjunction with the second composition. The swelling and expansion of the second composition, with its accompanying increase in volume, along with the simultaneous corresponding reduction in volume of the first composition, assures the delivery of beneficial agent through the osmotic passageway at a controlled rate over time.

Device 10 of FIGS. 1 through 4 can be made into many embodiments including the presently preferred embodiments for oral use for releasing a locally or systemically acting therapeutic agent in a gastrointestinal tract. Oral system 10 can have various conventional shapes and sizes, such as round with a diameter of 3/16 inches to ⅝ inches. In these forms system 10 can be adapted for administering beneficial agent to numerous animals, including warm blooded animals, humans, avians, reptiles and pisces.

FIGS. 5, 6 and 7 show another embodiment provided by this invention. FIGS. 5, 6 and 7 show an osmotic device 10 designed for placement in a body passageway, such as a vagina, or the ano-rectal canal. Device 10 has an elongated, cylindrical, self-sustaining shape with a curved lead end 20, a trailing end 21, and it is optionally equipped with manually controlled strings 22 for easily removing device 10 from the biological passageway. Device 10 is structurally identical with the device described above in FIGS. 1 through 4, and it operates in a like manner. In FIG. 5, device 10 is depicted with a semipermeable wall 23, in FIG. 6 with a laminated wall 24 comprising an inner semipermeable lamina 25 adjacent to compartment 14 and an external microporous lamina 26 distant from compartment 14. Micro porous lamina 26 can have preformed pores, or its pores can be formed when device 10 is in the environment of use, such as by leaching a leachable material from the lamina. The pores of lamina 26 are of controlled porosity size, and they can function as pore-passageways for the release of beneficial agent 15 from device 10. In FIG. 6, a pore controlled-releasing-passageway and a laser controlled-releasing-passageway function as the composite passageway 13 for releasing agent 15 from device 10. In FIG. 7, device 10 comprises a laminated wall 28 formed of a microporous lamina 29 next to compartment 14, and a semipermeable lamina 30 facing the environment of use and in laminar arrangement with microporous lamina 29. The semipermeable lamina used for manufacturing these osmotic devices is permselective since it is permeable to the passage of fluid and substantially impermeable to the passage of agent, osmagent and osmopolymer. The micropores of lamina 29 can align with the passage way of lamina 30 for releasing drug from device 10. Device 10 delivers a beneficial agent for absorption by the vaginal mucosa, or the anorectal mucosa, to produce an in vivo local or systemic effect over a prolonged period of time.

The devices of FIGS. 1 through 7 can be used for delivering numerous beneficial agents including drugs at a controlled rate independent of the drug pH dependency, or where the dissolution rate of the agent can vary between low and high in fluid environments, such as gastric fluid and intestinal fluid. The osmotic devices also provide for low/high loading of agents of low solubility and their delivery at meaningful, therapeutic amounts. While FIGS. 1 through 7 are illustrative of various devices that can be made according to the invention, it is to be understood these devices are not to be construed as limiting, as the devices can take a wide variety of shapes, sizes and forms adapted for delivering beneficial agents to the environment of use. For example, the devices include buccal, implant, rumen, artificial gland, cervical, intrauterine, ear, nose, dermal, vaginal, percutaneous, subcutaneous, anal, and like delivery devices. The devices also can be sized, shaped, structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions, and other environments of use.

DETAILED DESCRIPTION OF THE INVENTION

In accordance with the practice of this invention it has now been found that delivery device 10 can be manufactured with a first composition and a different second composition mutually housed in cooperative relationship in the compartment of the device. The compartment is formed by a wall comprising a material that does not adversely affect the beneficial agent, osmagent, osmopolymer, and the like. The wall is permeable to the passage of an external fluid such as water and biological fluids, and it is substantially impermeable to the passage of agents, osmagents, osmopolymers, and the like. The wall comprises a material that does not adversely affect an animal, or host, or the components comprising the device, and the selectively semipermeable materials used for forming the wall are non-erodible and they are insoluble in fluids. Typical materials for forming the wall are, in one embodiment, cellulose esters, cellulose ethers and cellulose ester-ethers. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono-, di- and tricellulose alkanylates; mono-, di- and tricellulose aroylates, and the like. Exemplary polymers include cellulose acetate having a D.S. up to 1 and an acetyl content up to 21%; cellulose acetate having an acetyl content of 32% to 39.8%; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propyl content of 39.2% to 45% and a hydroxyl content of 2.8% to 5.4%; cellulose acetate butyrate having a D.S. of 1.8, an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose triacylates having a D.S. of 2.9 to 3 such as cellulose trivalerate, cellulose trilaurate, cellulose tripalmitate, cellulose trisuccinate, and cellulose triocta noate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional polymers include ethyl cellulose of various degree of etherification with ethoxy content of from 40% to 55%, acetaldehyde dimethyl cellulose acetate, cellulose acetate ethyl carbamate, cellulose acetate methyl carbamate, cellulose acetate dimethyl aminoacetate, semipermeable polyamides; semipermeable polyurethanes; semipermeable sulfonated polystyrenes; semipermeable cross-linked selective polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); semipermeable cross-linked poly(vinylbenzyltrimethyl ammonium chloride); water permeable membrane exhibiting a fluid permeability of $2.5 \times 10^{-8}$ to $2.5 \times 10^{-4}$ (cm$^2$/hr·atm) expressed per atmosphere of hydrostatic or osmotic pressure difference across the wall. The polymers are known to the art in U.S. Pat. Nos. 3,845,770; 3,916,899; and 4,160,020; and in *Handbook of Common Polymers* by Scott, J. R.

and Roff, W. J., (1971), published by CRC Press, Cleveland, Ohio.

The laminated wall comprising a semipermeable lamina and a microporous lamina are in laminar arrangement and they act in concert to form an integral laminated wall that maintains its physical and chemical integrity and does not separate into the original lamina throughout the operative agent release history of the osmotic device. The semipermeable lamina is made from the semipermeable polymeric materials, the semipermeable homopolymers, and the semipermeable copolymers presented above, and the like.

Microporous lamina suitable for manufacturing a wall or a laminated osmotic device generally comprises preformed microporous polymeric materials, and polymeric materials that can form a microporous lamina in the environment of use. The microporous materials in both embodiments are laminated to form the laminated wall. The preformed materials suitable for forming the microporous lamina are essentially inert, they maintain their physical and chemical integrity during the period of agent release and they can be described generically as having a sponge like appearance that provides a supporting structure for a semipermeable lamina and also provides a supporting structure for microscopic sized interconnected pores or voids. The microporous materials can be isotropic wherein the structure is homogeneous throughout a cross sectional area, or they can be anisotropic wherein the structure is non-homogeneous throughout a cross sectional area. The pores can be continuous pores that have an opening on both faces of a microporous lamina, pores interconnected through tortuous paths of regular and irregular shapes, including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and the number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used for making a microporous lamina.

The pore size and other parameters characterizing the microporous structure also can be obtained from flow measurements, where a liquid flux, J, is produced by a pressure difference $\Delta P$, across the lamina. The liquid flux through a lamina with pores of uniform radius extended through the lamina and perpendicular to its surface with area A given by relation (13):

$$J = \frac{N\pi r^4 \Delta P}{8\eta \Delta x} \quad (13)$$

wherein J is the volume transported per unit time and lamina area containing N number of pores of radius r, $\eta$ is the viscosity of the liquid and $\Delta P$ is the pressure difference across the lamina with thickness $\Delta x$. For this type of lamina, the number of pores N can be calculated from relation (14), wherein $\epsilon$ is the porosity defined as the ratio of void volume to total volume of the lamina; and A is the cross sectional area of the lamina containing N pores.

$$N = \frac{\epsilon A}{\pi r^2} \quad (14)$$

The pore radius then is calculated from relation (15):

$$r = \left[ 8\eta \frac{\Delta x \cdot \tau}{\Delta P \cdot \epsilon} J' \right]^{\frac{1}{2}} \quad (15)$$

wherein J' is the volume flux through the lamina per unit area pro duced by the pressure difference $\Delta P$ across the lamina, $\eta$, $\epsilon$ and $\Delta x$ have the meaning defined above and $\tau$ is the tortuosity defined as the ratio of the diffusional path length in the lamina to the lamina thickness. Relations of the above type are discussed in *Transport Phenomena In Membranes*, by Lakshminatayanaiah, N. Chapter 6, (1969), published by Academic Press, Inc., New York.

As discussed in this reference, supra, on page 336, in Table 6.13, the porosity of the lamina having pores with radius r can be expressed relative to the size of the transported molecule having a radius a, and as the ratio of molecular radius to pore radius a/r decreases, the lamina becomes porous with respect to this molecule. That is, when the ratio a/r is less than 0.3, the lamina becomes substantially microporous as expressed by the osmotic reflection coefficient $\sigma$ which decreases below 0.5. Microporous lamina with a reflection coefficient $\sigma$ in the range of less than 1, usually from 0 to 0.5, and preferably less than 0.1 with respect to the active agent are suitable for fabricating the system. The reflection coefficient is determined by shaping the material in the form of a lamina and car rying out water flux measurements as a function of hydrostatic pressure difference and as a function of the osmotic pressure difference caused by the active agent. The osmotic pressure difference creates a hydrostatic volume flux, and the reflection coefficient is expressed by relation (16):

$$\sigma = \frac{\text{osmotic volume flux}}{\text{hydrostatic volume flux}} \quad (16)$$

Properties of microporous materials are described in *Science*, Vol. 170, pp 1302-1305, (1970); *Nature*, Vol. 214, page 285, (1967); *Polymer Engineering and Science*, Vol. 11, pp 284–288, (1971); U.S. Pat. Nos. 3,567,809 and 3,751,536; and in *Industrial Processing With Membranes*, by Lacey, R. E., and Loeb, Sidney, pp 131–134, (1972).

Microporous materials having a preformed structure are commercially available and they can be made by art known methods. The microporous materials can be made by etching, nuclear tracking, by cooling a solution of flowable polymer below the freezing point whereby solvent evaporates from the solution in the form of crystals dis persed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte process. Process for repairing microporous materials are described in *Synthetic Polymer Membranes*, by R. E. Kesting, (1971), Chapters 4 and 5, published by McGraw Hill, Inc; *Chemical Reviews*, "Ultrafiltration", Vol. 18, pp 373 to 455, (1934); *Polymer Eng. and Sci.*, Vol. 11, No. 4, pp 284–288, (1971); *J. Appl. Poly. Sci.*, Vol. 15, pp 811–829, (1971); and in U.S. Pat. Nos. 3,565,259; 3,615,024; 3,751,536; 3,801,692; 3,852,224, and 3,849,528.

Microporous materials useful for making the wall or the lamina include microporous polycarbonates comprised of linear polyesters of carbonic acid in which carbonate groups recur in the polymer chain; microporous materials prepared by the phosgenation of a dihydroxyl aromatic, such as bisphenol A; microporous poly(vinyl chloride); microporous polyamides such as polyhexamethylene adipamide; microporous modacrylic copolymers including those formed from 60% vinyl chloride and 40% acrylonitrile; styrene acrylic copolymers; porous polysulfones characterized by diphenylene sulfone groups in a linear chain thereof; poly(vinylidene) halides; polychloroethers; acetal polymers; polyesters prepared by esterification of a dicarboxylic acid or anhydride with an alkylene polyol; poly(alkylenesulfides); phenolic polyesters; microporous poly(saccharides); microporous polymers having substituted and unsubstituted anhydroglucose units exhibiting a higher permeability to the passage of water and biological fluids than a semipermeable lamina; asymmetric porous polymers; cross linked olefin polymers; hydrophobic or hydrophilic microporous homopolymers, copolymers or interpolymers having a reduced bulk density; and materials described in U.S. Pat. Nos. 3,597,752; 3,643,178; 3,654,066; 3,709,774; 3,718,532; 3,803,061; 3,852,224; 3,853,601; and 3,852,388, in British Patent No. 1,126,849, and in *Chem. Abst.*, Vol. 71 4274F, 22572F, 22573F, (1969).

Additional microporous materials include microporous poly(urethanes); microporous cross linked, chain extended poly(urethanes); microporous poly(urethanes) in U.S. Pat. No. 3,524,753; microporous poly(imides); microporous poly(benzimidazoles); regene rated microporous proteins; semi-solid cross linked microporous poly(vinylpyrrolidone); microporous materials prepared by diffusion of multivalent cations into polyelectrolyte sols as in U.S. Pat. No. 3,565,259; anisotropic microporous materials of ionically associated polyelectrolytes; porous polymers formed by the coprecipitation of a polycation and a polyanion as described in U.S. Pat. Nos. 3,276,589; 3,541,055; 3,541,066 and 3,546,142; deriva tives of poly(styrene), such as microporous poly(sodium styrenesulfonate) and microporous poly(vinyl benzyltrimethyl-ammonium chloride), the microporous materials disclosed in U.S. Pat. Nos. 3,615,024, U.S. Pat. Nos. 3,646,178, 3,852,224, and the like.

Further, the micropore forming material used for the purpose of the invention includes the embodiment wherein the microporous wall or the lamina is formed in situ by a pore former being removed by dissolving, extracting, eroding, or leaching it to form the microporous lamina during the operation of the system. The pore former can be a solid or a liquid. The term, "liquid," for this invention, embraces semi-solids and viscous fluids. The pore formers can be inorganic or organic. The pore formers suitable for the invention include pore formers that can be extracted, dissolved or leached without any chemical change in the polymer. The pore forming solids have a size of about 0.1 to 200 micrometers and they include alkali metal salts such as sodium chloride, sodium bromide, potassium chloride, potassium sulfate, potassium phosphate, sodium benzoate, sodium acetate, sodium citrate, potassium nitrate, and the like. The alkali earth metal salts include calcium phosphate, calcium nitrate and the like. The transition metal salts include ferric chloride, ferrous sulfate, zinc sulfate, cupric chloride, manganese fluoride, manganese fluorosilicate, and the like. The pore formers include organic compounds such as polysaccharides. The polysaccharides include the sugars: sucrose, glucose, fructose, mannose, galactose, aldohexose, altrose, talose, lactose, monosaccharides and disaccharides; and polyalcohols such as mannitol and sorbitol. Also, organic aliphatic and aromatic oils and solids, including diols and polyols, as exemplified by polyhydric alcohols, poly(alkylene glycols), polyglycols, alkylene glycols, poly(alpha-omega)-alkylene diols esters or alkylene glycols and the like; water soluble cellulosic polymers such as hydroxyloweralkyl cellulose, hydroxypropylmethylcellulose, methylcellulose, methylethyl cellulose, hydroxyethylcellulose and the like: water soluble polymers such as sodium carboxymethylcellulose and the like. The pore-formers on their removal from the lamina form channels through the lamina. These can serve as pore-passageways for effective release of agent from the system. In a preferred embodiment the nontoxic, pore forming agents are selected from the group consisting of inorganic and organic salts, carbohydrates, polyalkylene glycols, poly (alpha-omega)-alkylenediols, esters of alkylene glycols, glycols, alcohols, hydric alcohols, and water soluble polymers used for forming a microporous lamina in a biological environment. Generally, for the purpose of this invention, when the polymer forming the microporous lamina contains more than 15% by weight of a pore former, the polymer is a precursor microporous lamina that on removing the pore former yields a lamina which is substantially microporous.

The expression, "passageway," as used herein comprises means and methods suitable for releasing the agent or drug from the osmotic system. The expression, "passageway," includes aperture, orifice, hole, porous element, hollow fiber, capillary tube, microporous insert, pore, microporous overlay, or bore, and the like, through the semipermeable lamina, the microporous lamina, or through the laminated wall. The passageway can be formed by mechanical drilling, laser drilling, eroding an erodible element, extracting, dissolving, bursting or leaching a passageway former from the wall. One description of a presently preferred passageway an the maximum and minimum dimensions for such a passageway, are disclosed in U.S. Pat. Nos. 3,845,770 and 3,916,899. The osmotically calibrated passageway has a maximum cross sectional area, $A_s$, defined by the relation (17) as follows:

$$A_{s(max)} = \frac{L}{F} \times \frac{Q_p}{t} \times \frac{1}{DS} \quad (17)$$

wherein L is the length of the passageway $Q_p/t$ is the mass delivery rate of the agent, D is the diffusion coefficient of the agent, S is the solubility of the agent in the fluid, and F is from 2 to 1000, said passageway having a minimum area $A_s$ defined by relation (18) as follows:

$$A_{s(min)} = \left[ \frac{Lv}{t} \times 8 \times \frac{\pi\eta}{\Delta P} \right]^{\frac{1}{2}} \quad (18)$$

wherein L is the length of the passageway, v/t is the agent solution volume delivery rate, $\pi$ is 3.14; $\eta$ is the viscosity of agent solution or suspension dispensed from the device and ΔP is the hydrostatic pressure difference between the inside and the outside of the compartment having a value up to 20 atmospheres. In addition, one or more passageways can be introduced into the device. The number of passageways can be large, but should satisfy the condition that the delivery rate is substantially governed by the imbibition flux of water across the surrounding wall.

The passageway can be a pore formed by leaching sorbitol, and the like, from a wall, as disclosed in U.S. Pat. No. 4,200,098. This patent discloses pores of controlled size-porosity formed by dissolving, extracting or leaching a material from a wall, such as sorbitol from cellulose acetate. The pore-passageways extend from the inside to the outside of the wall for effective release of beneficial agent including a drug to the exterior of the system. In U.S. Pat. No. 4,285,987 a composite delivery system is disclosed comprising a first device that surround a second device. The first comprises a cellulose acetate wall comprising leachable sorbitol for forming a pore for releasing osmotically active potassium chloride from an osmotic core. The second device releases drug through a laser drilled passageway. The patent thereby discloses drug released through passageways formed by different techniques.

The osmotically effective compounds that can be used for the purpose of this invention include inorganic and organic compounds that exhibit an osmotic pressure gradient across a semipermeable wall, or across a microporous, or a laminated wall, against an external fluid. The osmoticlly effective compounds, along with the osmopolymers, imbibe fluid into the osmotic device thereby making available in situ fluid for imbibition and/or absorption by an osmopolymer to enhance its expansion, and/or for forming a solution or suspension containing a beneficial agent for its delivery through a passageway form the osmotic device.

The osmotically effective compounds are known also as osmotically effective solutes, and also as osmagents. The osmotically effective compounds are used by mixing them with a beneficial agent, or with an osmopolymer for forming a solution, or suspension containing the beneficial agent that is osmotically delivered from the device. The expression, "limited solubility," as used herein means the agent has a solubility of about less than 5% by weight in the aqueous fluid present in the environment. The osmotic solutes are used by homogeneously or heterogeneously mixing the solute with the agent or osmopolymer and then charging them into the reservoir. The solutes and osmopolymers attract fluid into the reservoir producing a solution of solute in a gel which is delivered from the system concomitantly transporting undissolved and dissolved beneficial agent to the exterior of the system. Osmotically effective solutes used for the former purpose include magnesium sulfate, magnesium chloride, potassium sulfate, sodium sulfate, lithium sulfate, potassium acid phosphate, d-mannitol, urea, inositol, magnesium succinate, tartaric acid, carbohydrates such as raffinose, sucrose, glucose, alpha-d-lactose monohydrate, sorbitol, and mixtures thereof. The amount of osmagent in the compartment will generally be from 0.01% to 30% or higher in the first composition, and usually from 0.01% to 40% or higher in the second composition.

The osmotic solute is preferably initially present in excess and it can be in any physical form that is compatible with the beneficial agent, the device, and the osmopolymer. The osmotic pressure of saturated solutions of various osmotically effective compounds and for mixtures of compounds at 37° C., in water, are listed in Table 1. In the table, the osmotic pressure $\pi$, is in atmospheres, atm. The osmotic pressure is measured in a commercially available osmometer that measures the vapor pressure difference between pure water and the solution to be analyzed and, according to standard thermodynamic principles, the vapor pressure ratio is converted into osmotic pressure difference. In Table 1, osmotic pressures of from 20 atm to 500 atm are set forth. Of course, the invention includes the use of lower osmotic pressures from zero, and higher osmotic pressures than those set forth by way of example in Table 1. The osmometer used for the present measurements is identified as Model 320B, Vapor Pressure Osmometer, manufactured by the Hewlett Packard Co., Avondale, Pa.

TABLE 1

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Manitol-Sucrose | 170 |
| Dextrose | 82 |
| Potassium Sulfate | 39 |
| Mannitol | 38 |
| Sodium Phosphate Tribasic 12H$_2$O | 36 |
| Sodium Phosphate Dibasic 7 H$_2$O | 31 |
| Sodium Phosphate Dibasic 12H$_2$O | 31 |
| Sodium Phosphate Dibasic Anhydrous | 29 |
| Sodium Phosphate Monobasic H$_2$O | 28 |

The osmopolymers suitable for forming the first drug containing osmotic composition, and also suitable for forming the second drug free osmotic composition, are osmopolymers that exhibit fluid imbibition properties. The osmopolymers are swellable, hydrophilic hydrogel polymers which osmopolymers interact with water and aqueous biological fluids and swell or expand to an equilibrium state. The osmopolymers exhibit the ability to swell in water and retain a significant portion of the imbibed water within the polymer structure. The osmopolymers swell or expand to a very high degree, usually exhibiting a 2 to 50 fold volume increase. The osmopolymers can be noncross-linked or cross-linked. The swellable, hydrophilic polymers are, in one presently preferred embodiment, lightly cross-linked, such cross-links being formed by covalent bonds, hydrogen bonds, ionic bonds or residue crystalline regions after swelling. The osmopolymers can be of plant, animal or synthetic origin. The osmopolymers are hydrophilic polymers. Hydrophilic polymers suitable for the present purpose include poly(hydroxy-alkyl methacrylate) having a molecular weight of from 30,000 to 5,000,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methylcellulose, cross-linked agar and carboxymethyl cellulose; a mixture of hydroxypropyl methylcellulose and sodium carboxymethylcellulose, hydroxypropyl-methylcellulose and sodium carboxymethyl cellulose; a water insoluble, water swellable copolymer reduced by forming a dispersion of finely divided copolymer of maleic anhydride with styrene, ethylene, propylene, butylene or isobutylene crosslinked with from 0.001 to about 0.5 moles of saturated cross-linking agent per mole of maleic anhydride in copolymer; water swellable polymers of N-vinyl lactams; polyoxyethylene-polyoxypropylene gel; polyoxybutylene-polyethylene block copolymer gel; carob gum, polyacrylic gel; polyester gel; polyurea gel; polyether gel; polyamide gel; polyimide gel; polypeptide gel; polyamino acid gel; polycellulosic gel; polygum gel; initially dry hydrogels that generally imbibe and absorb water which penetrates the glassy hydrogel and lowers its glass transition temperature, and the like.

Other osmopolymers include hydrogels such as Carbopol ® acidic carboxy polymers, a polymer of acrylic acid crosslinked with a polyallyl sucrose, also known as carboxypolymethylene and carboxyvinyl polymer having a molecular weight of 250,000 to 4,000,000; Cyanamer ® polyacrylamides; cross-linked water swellable indene-maleic anhydride hydrogel polymers; Goodrite ® polyacrylic acid having a molecular weight of 80,000 to 200,000; Polyox ® polyethylene oxide polymers having a molecular weight of 100,000 to 5,000,000 and higher; starch graft copolymers; Aqua-Keeps ® acrylate polymer polysaccharides composed of condensed glucose units such as diester cross-linked polyglucan; and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in *Handbook of Common Polymers*, by Scott and Roff, published by the Chemical Rubber Company, Cleveland, Ohio. The amount of osmopolymer in the first composition is about 10% to 90%, and the amount of osmopolymer in the second composition is 20% to 100%, with the total weight of all ingredients in a composition equal to 100%. In a presently preferred embodiment, the osmopolymer identified as $P_1$ comprising the first composition is different than the osmopolymer identified as $P_2$ comprising the second composition. The osmopolymer in the first composition can be structurally different than the osmopolymer in the second composition. Or, the osmopolymer's molecular weight in the second osmotic composition is larger than the molecular weight of the osmopolymer in the first composition. The osmopolymer $P_1$ comprising the first composition comprising the beneficial agent serves as a pharmaceutically acceptable carrier for transporting the active agent from the device in the form of a paste or gel-like ribbon, and it also contributes to the driving force that cooperates with osmopolymer $P_2$ comprising the second composition that delivers the agent through the passageway from the device. The phrase, "pharmaceutically acceptable carrier," as used for the purpose of this invention, means the drug is mixed with a gel and is transported with the gel from the device. During operation of the device fluid is imbibed into the device resulting in the viscosity of $P_2$ being greater than the viscosity of $P_1$. In this operation $P_1$ and $P_2$ operate as a single unit substantially free of a void between their interfaced contacting surfaces of osmopolymer $P_1$ and $P_2$ for successful delivery of the beneficial agent from the osmotic device.

Osmopolymer fluid imbibition determination for a chosen polymer can be made by following the procedure described below. A round die having an inner diameter of ½ inch, fitted with a ½ inch diameter stainless steel plug, is charged with a known quantity of polymer with the plugs extending out either end. The plugs and the die were placed in a Carver press with plates between 200° F. and 300° F. A pressure of 10,000 to 15,000 psi was applied to the plugs. After 10 to 20 minutes of heat and pressure the electrical heating to the plates was turned off, and tap water circulated through the plates. The resulting ½ inch disks were placed in an air suspension coater charged with 1.8 kg saccharide cores, placebo cores, made of any sugar such as lactose, and so forth, and coated with cellulose acetate having an acetyl content of 39.8% dissolved in 94:6 w/w, $CH_2Cl_2/CH_3OH$, to yield a 3% w/w solution. The coated systems were dried overnight at 50° C. The coated disks were immersed in water at 37° C. and periodically removed for a gravimetric determination of water imbibed. The initial imbibition pressure was calculated by using the water transmission constant for the cellulose acetate, after normalizing imbibition values for membrane surface area and thickness. The polymer used in this determination was the sodium derivative of Carbopol-934 ® polymer, prepared according to the procedure of B. F. Goodrich Service Bulletin GC-36, "Carbopol ® Water-Soluble Resins," page 5, published by B. F. Goodrich, Akron, Ohio.

The cumulative weight gain values, y, as a function of time, t, for the water soluble polymer disk coated with the cellulose acetate were used to determine the equation of the line $y = c + bt + at^2$ passing through those points by at least square fitting technique.

The weight gain for the sodium salt of Carbopol-934 ® is given by the equation (19) that follows: Weight gain equals $0.359 + 0.665t - 0.00106t^2$ wherein t is elapsed time in minutes. The rate of water flux at any time will be equal to the slope of the line that is given by the following equations (19) and (20):

$$\frac{dy}{dt} = \frac{d(0.359 + 0.665t - 0.00106t^2)}{dt} \quad (19)$$

$$\frac{dy}{dt} = 0.665 = 0.00412t \quad (20)$$

To determine the initial rate of water flux the derivative is evaluated at $t = 0$, and $dy/dt$ 0.665 µl/min., which is equal to the coefficient b. Then, normalizing the imbibition rate for time, membrane surface area and thickness, and the membrane permeability constant to water, $K\pi$ may be determined according to the following equation (21):

$$K\pi = 0.665 \, \mu l/min \times \left(\frac{60 \text{ min}}{\text{hr}}\right) \times \left(\frac{1 \text{ ml}}{1000 \, \mu l}\right) \left(\frac{0.008 \text{ cm}}{2.86 \text{ cm}^2}\right) \quad (21)$$

with $K\pi = 1.13 \times 10^{-4}$ cm$^2$/hr. The $\pi$ value for NaCl was determined with a Hewlett Packard vapor pressure osmometer to be 345 atm ± 10%, and the K value for cellulose acetate used in this experiment calculated from NaCl imbibition values was determined to be $1.9 \times 10^{-7}$ cm$^2$/hr·atm.

Substituting these values into the calculated $K\pi$ expression, $(1.9 \times 10^{-7}/\text{cm}^2/\text{hr atm})(\pi) = 1.13 \times 10^{-4}$ cm$^2$hr gives $\pi = 600$ atm at $t = 0$. As a method for evaluating the efficiency of a polymer with respect to duration of zero order driving force, the percent of water uptake was selected before the water flux values decreased to 90% of their initial values. The value of the slope for the equation of a straight line emanating from the percent weight gained axis will be equal to the initial value of dy/dt evaluated at t=0, with the y intercept c defining the linear swelling time, with (dy/dt) 0=0.665 and the y intercept=0, which yields y=0.665t+0.359. In order to determine when the value of the cumulative water uptake is 90% below the initial rate, the following expression is solved for t:

$$0.9 = \frac{at^2 + bt + c}{bt + c} = \frac{\Delta W}{w} 0.9 \qquad (22)$$

$$\frac{0.00106\ t^2 + 0.665\ t + 0.359}{0.665\ t + 0.359} = 0.9 \qquad (23)$$

and solving for t, $$-0.00106\ t^2 + 0.0065\ t + 0.0359 = 0$$

$$t = \frac{-0.0665 + [(0.0665)^2 - 4(-0.00106)(0.0359)]^{\frac{1}{2}}}{2(-0.00106)} \qquad (24)$$

t=62 min and the weight gain is $-0.00106(62)^2 + (0.665)(62) + 0.359\ 38\ \mu l$, with the initial sample weight=100 mg, thus ($\Delta w/w$) 0.9×100=38%. The results are presented in FIG. 8 for a graphical representation of the values. Other methods available for studying the hydrogel solution interface include rheologic analysis, viscometric analysis, ellipsometry, contact angle measurements, electrokinetic determinations, infrared spectroscopy, optical microscopy, interface morphology and microscopic examination of an operative device.

The expression, "beneficial agent," as used herein, includes any beneficial agent, or beneficial compound, that can be delivered from the device to produce a beneficial and useful therapeutic result. The beneficial agent can be insoluble to very soluble in the exterior fluid that enters the device and it optionally can be mixed with an osmotically effective compound and an osmopolymer. The term, "beneficial agent," includes algicide, antioxidant, air purifier, biocide, bactericide, catalyst, chemical reactant, disinfectant, fungicide, fermentation agent, fertility inhibitor, fertility promoter, germicide, plant growth promoter, plant growth inhibitor, preservative, rodenticide, sterilization agent, sex sterilant, and the like.

In the specification and the accompanying claims, the term, "beneficial agent," also includes drug. The term, "drug," includes any physiologically or pharmacologically active substance that produces a local or systemic effect, in animals, including warm-blooded mammals, humans and primates; avians; household, sport and farm animals; laboratory animals; fishes; reptiles and zoo animals. The term, "physiologically," as used herein, denotes the administration of a drug to produce generally normal levels and functions. The term, "pharmacologically," denotes generally variations in response to the amount of drug administered to the host. See *Stedman's Medical Dictionary*, (1966), published by Williams and Wilkins, Baltimore, MD. The phrase, "drug formulation," as used herein, means the drug is in the compartment mixed with the osmopolymer and, if applicable, with a binder and optional lubricant. The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autacoid systems, alimentary and excretory systems, inhibitory of autocoid systems, alimentary and excretory systems, inhibitory of autocoids and histamine systems. The active drug that can be delivered for acting on these recipients include anticonvulsants, analgesics, anti-inflammatories, calcium antagonists, anesthetics, antimicrobials, antimalarials, antiparasitic, antihypertensives, antihistamines, antipyretics, alpha-adrenergic agnoist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Exemplary drugs that are very soluble in water and can be delivered by the osmotic devices of this invention include prochlor perazine edisylate, ferrous sulfate, aminocaproic acid, potassium chloride, mecamylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, and the like.

Exemplary drugs that are poorly soluble in water and that can be delivered by the devices of this invention include diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendro-flumethiazide, chlorpropamide, tolazamide, chlormadinone acetate, phenaglycodol, allopurinol, aluminum aspirin, methotrexate, acetyl sulfisoxazole, erythromycin, progestins, sterogenic, progestational, corticosteroids, hydrocortisone hydrocorticosterone acetate, cortisone acetate, triamcinolone, methyltesterone, 17 beta-estradiol, ethinyl estradiol, ethinyl estradiol 3-methyl ether, pednisolone, 17 beta-hydroxyprogesterone acetate, 19-nor-progesterone, norgestrel, norethindrone, norethisterone, norethiederone, progesterone, norgesterone, norethynodrel, and the like.

Examples of other drugs that can be delivered by the osmotic device include aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chloropromazine, methyldopa, dihydroxyphenylalanine, pivaloyloxyethyl ester of alpha-methyldopa hydrochloride, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, madol, quanbenz, hydrochlorothiazide, ranitidine, flurbiprofen, fenbufen, fluprofen, tolmetin, alolofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, captopril, ramipril, endlapriat, famotidine, nizatidine, sucralfate, etintidine, tertatolol, minoxidil, chlordiazepoxide, chlordiazepoxide hydrochloride, diazepan, amitriptylin hydrochloride, impramine hydrochloride, imipramine pamoate, enitabas, and the like. The beneficial drugs are known to the art in *Pharmaceutical Sciences*, 14th Ed., edited by Remington, (1979) published by Mack publishing Co., Easton, Pa.; *The Drug, The Nurse, The Patient, Including Current Drug Handbook*, by Falconer, et al., (1974–1976) published by Saunders Company, Philadelphia, Pa.; *Medicinal Chemistry*, 3rd Ed., Vol. 1 and 2, by Burger, published by Wiley-Interscience, New York; and in *Physicians' Desk Reference*, 38th Ed., (1984) published by Medical Economics Co., Oradell, N.J.

The drug can be in various forms, such as uncharged molecules, molecular complexes, pharmacologically acceptable salts such as hydrochloride, hydrobromide, sulfate, laurate, palmitate, phosphate, nitrite, borate, acetate, maleate, tartrate, oleate and salicylate. For acidic drugs, salts of metals, amines or organic cations; for example, quarternary ammonium can be used. Derivatives of drugs such as ester, ethers and amides can be used. Also, a drug that is water insoluble can be used in a form that is water soluble derivative thereof to serve as a solute, and on its release from the device, is converted by enzymes, hydrolyzed by body pH or other metabolic processes to the original biologically active form. The agent, including drug, can be present in the compartment with a binder, dispersant, wetting agent, suspending agent, lubricant and dye. Representative of these include suspending agents such as acacia, agar, calcium carrageenan, alginic acid, algin, agarose powder, collagen, colloidal magnesium silicate, pectin, gelatin and the like; binders like polyvinyl pyrrolidone, lubricants such as magnesium stearate; wetting agents such as fatty amines, fatty quaternary ammonium salts, and the like. The phrase, "drug formulation," indicates the drug is present in the compartment accompanied by an osmagent, osmopolymer, a binder, and/or the like. The amount of beneficial agent in a device generally is about from 0.05 ng to 5 g or more, with individual devices containing, for example, 25 ng, 1 mg, 5 mg, 10 mg, 25 mg, 125 mg, 250 mg, 500 mg, 750 mg, 1.0 g, 1.2 g, 1.5 g, and the like. The devices can be administered one, twice or thrice daily.

The solubility of a beneficial agent in the fluid can be determined by known techniques. One method consists of preparing a saturated solution comprising the fluid plus the agent as ascertained by analyzing the amount of agent present in a definite quantity of the fluid. A sample apparatus for this purpose consists of a test tube of medium size fastened upright in a water bath maintained at constant temperature and pressure, in which the fluid and agent are placed and stirred by a rotating glass spiral. After a given period of stirring, a weight of the fluid is analyzed and the stirring continued and additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound option ally may be not needed; if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in the *United States Public Health Service Bulletin*, No. 67 of the Hygienic Laboratory; *Encyclopedia of Science and Technology*, Vol. 12, pp 542 to 556, (1971) published by McGraw-Hill, Inc.; and *Encyclopedia Dictionary of Physics*, Vol. 6, pp 547 to 557, (1962) published in Pergamon Press, Inc.

The device of the invention is manufactured by standard techniques. For example, in one embodiment the beneficial agent is mixed with an osmagent and osmopolymer, and pressed into a solid possessing dimensions that correspond to the internal dimensions of the compartment adjacent to the passageway; or the beneficial agent and other formulation forming ingredients and a solvent are mixed into a solid or a semisolid by conventional methods such as ballmilling, calendering, stirring or rollmilling, and then pressed into a preselected shape. Next, a layer of a composition comprising an osmagent and an osmopolymer is laced in contact with the layer of beneficial agent formulation, and the two layers surrounded with a semipermeable wall. The layering of the beneficial agent composition and the osmagent/osmopolymer can be accomplished by conventional two layer tablet press techniques. The wall can be applied by molding, spraying, or dipping the pressed shapes into wall-forming materials. Another and presently preferred technique that can be used for applying the wall is the air suspension coating procedure. This procedure consists in suspending and tumbling the pressed compositions in a current of air and a wall forming composition until the wall surrounds and coats the two pressed compositions. They form a laminated wall. The air suspension procedure is described in U.S. Pat. No. 2,799,241; *J. Am. Pharm. Assoc.*, Vol. 48, pp 451 to 459 (1979); and, *ibid*, Vol. 49, pp 82 to 84 (1960). Other standard manufacturing procedures are described in *Modern Plastics Encyclopedia*, Vol. 46, pp 62 to 70 (1969); and in *Pharmaceutical Science*, by Remington, 14th Ed., pp 1626 to 1978 (1970), published by Mack Publishing Co., Easton, Pa.

Exemplary solvents suitable for manufacturing the wall, the laminates and laminae, include inert inorganic and organic solvents, that do not adversely harm the materials and the final wall or the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DESCRIPTION OF EXAMPLES

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

The operation of a device 10 manufactured according to the invention is set forth in this example. The volume imbibition rate of the push formulation composition is equal to the volume rate of water imbibition (dV/dt)p into the osmotic push agent formulation composition expressed by equation (25) as follows:

$$\left(\frac{dV}{dt}\right)_p = \frac{k}{h} A_p \cdot \Delta\pi \quad (25)$$

where k is the water permeability of the semipermeable wall, h is the thickness of the wall, $A_p$ is the wall surface of the push compartment exposed to the osmotic process, and $\Delta\pi$ is the osmotic pressure difference of the push formulation across the wall. The geometrical shape considered here is as shown in FIG. 5, with flat bottom and cylindrical body. The volume rate of water imbibition can be related to the total surface area for water transport A from the end and cylindrical sections from equations (26) and (27):

$$A_p = \Delta r^2 + 2\, rl \quad (26)$$

where l is the height of the osmotic formulation.

$$A_p = \pi r^2 + \frac{2}{r} V \quad (27)$$

where V is the volume of osmotic formulation. The volume expansion of the osmotic driving member equals $$V = V_o + V_H \quad (28)$$

where $V_o$ and $V_H$ are, respectively, the volumes of dry osmotic agent formulation and water imbibed. Alternatively, (28) can be written $$V = \frac{W_o}{\rho_o} + \frac{W_H}{\rho_H} \quad (29)$$

where $\rho_o$ is the density of dry osmotic agent formulation, $W_o$ and $W_H$ are the weights of osmotic agent and water imbibed, and $\rho_H$ is the density of water.

Rearranging terms within the equations, the following equation results:

$$V = \frac{W_o}{\rho_o}\left(1 + \frac{W_H}{W_o} \cdot \frac{\rho_o}{\rho_H}\right) \quad (30)$$

and $$A_p = \pi r^2 + \frac{2}{r} \frac{W_o}{\rho_o}\left(1 + \frac{W_H}{W_o} \cdot \frac{\rho_o}{\rho_H}\right) \quad (31)$$

Therefore, the volume rate of water imbibition is expressed by:

$$\left(\frac{dV}{dt}\right)_p = \frac{k}{h}\left\{\pi r^2 + \frac{2}{r}\left(1 + \frac{\rho_o}{\rho_H} \frac{W_H}{W_o}\right)\frac{W_o}{\rho_o}\right\}\Delta\pi \quad (32)$$

The release rate of drug from the dispenser can be written as shown in equation (3) where F and Q are respectively the volume flow into the drug and osmotic push compartment.

$$\frac{dm}{dt} = (F + Q)\, C_d \quad (33)$$

Here $C_d$ is the concentration of drug in the dispensed formulation. Equation (33) considered in conjunction with (32), allow for numerous delivery rates and drug programs derived from system 10 geometry and the osmotic pressure $\Delta\pi$ programmed in the dispenser as a function of time.

For development of the example, equation (34) will be substituted in the subsequent equations.

$$H = \frac{W_H}{W_o} \quad (34)$$

The composition of the driving push composition is formulated with an osmotically active polymer composition as shown in FIG. 9 which exhibits an osmotic pressure as a function of hydration as shown for membranes of two pumping rates. The osmotic pressure can be described by equations (35) and (36).

$$\Delta\pi = 180 \text{ atm for } H \leq 0.15 \quad (35)$$

$$\Delta\pi = 227 \exp(-0.332\, H) \text{ for } H > 0.15 \quad (36)$$

Substituting equation (36) and equation (37) in equation (25) equation (38) results as follows:

$$A_p(H)\pi r^2 + \frac{2}{r}\left(1 + \frac{\rho_o}{\rho_H} H\right)\frac{W_o}{\rho_o} \quad (37)$$

$$\left(\frac{dV}{dt}\right)_p = \frac{k}{h} \cdot A_p(H) \cdot \Delta\pi(H) \quad (38)$$

In addition, equation (39) holds for the volume of absorbed water $V_H$ $$V_H = \frac{W_H}{\rho_H} = H \cdot \frac{W_o}{\rho_H} \quad (39)$$

Since the volume of formulation displaced equation (40) is related to H by equation (39), $$\left(\frac{dV}{dt}\right)_p = \frac{dV_H}{dt} \quad (40)$$

it follows that equation (41) results $$\frac{dH}{dt} = \frac{\rho H}{W_o} \cdot \frac{k}{h} \cdot A_p(H) \cdot \Delta\pi(H) = f(H) \quad (41)$$

The solution of this differential equation will result in H(t) which can be substituted in equation (38) to yield the release rate. The solution to equation (41) was solved by numerical integration, resulting in the simulations for the release rates given by the numerical integration of equation (41) is obtained from equation (42) as follows:

$$= \int_o^H \frac{dH}{f(H)} = \int_o^t dt \quad (42)$$

The final value at shutdown for system 10 for $H_f$ and $t_f$ is given by equation (43):

$$H_f \frac{\rho H}{\rho_{dc}} \cdot \frac{W_{dc}}{W_o} \quad (43)$$

Here $\pi_{dc}$ and $W_{dc}$ are the density and weight of the drug composition. The function H(t) is obtained by finding the time $t_i$ associated with the hydration value $H_i$. The final value of H, $H_f$ equation (43) can be reached after m equal steps $\Delta H$, such that equation (44) results, and also equation (45).

$$\Delta H_j = \frac{H_f}{m} \quad (44)$$

$$H(t_i) = \sum_{j=i}^{i} \Delta H_j \quad (45)$$

The time $t_i$ associated with $H_i$ is calculated from equation (46) where $\overline{f(H_j)}$ average value of expression (41) between the start and end of the interval i:

$$t_i = \sum_{j=1}^{i} \Delta t_j \quad (46)$$

Here $\Delta t_j$ is given by (47)

$$\Delta t_j = \frac{\Delta H_j}{\overline{F(H)_j}} \quad (47)$$

From equations (39), (40), and (47), it follows then that the volume push rate $$\left(\frac{dV}{dt}\right)_p (t)$$

as a function of time is given by equation (48).

$$\left(\frac{\Delta V}{\Delta t}\right)_p (t) = \frac{W_o}{\rho H} \cdot \frac{\Delta H_i}{\Delta t_i} \quad (48)$$

The concentration $C_d$ of drug in the dispensed formulation can be written as shown in equation (49) where $C_o$ is the $$C_d = C_o \cdot F_D \quad (49)$$

concentration of solids dispensed and $F_D$ the fraction of drug in the dispensed formulation. This fraction of drug $F_D$ can assume to be equal to the fraction of drug formulated in the drug compartment in the dry state if the drug formulation is dispensed uniformly; $\pi_{dc}$ is the density of the drug formulation.

These push-pull systems operate favorably in a region where the drug compartment formulates drug in suspension at a constant rate and wherein the push compartment dispenses this formulation at a constant rate. Such condition is achieved when the majority of semisolid drug formulation is dispensed such that the total drug delivery rate can be expressed by equation (50).

$$\frac{dm}{dt} = \left(\frac{dV}{dt}\right)_p F_D \cdot \rho_{dc} \quad (50)$$

The influx of water in the drug compartment $$F = \left(\frac{dV}{dt}\right)_D$$

is responsible for converting the solid drug formulation into a fluid form of drug concentration $C_d$. The volume flux F adds to the osmotic driving flux $$Q = \left(\frac{dV}{dt}\right)_p$$

yield equation (51).

$$\frac{dm}{dt} = (Q + F) \cdot C_d \quad (51)$$

By equating equations (33) and (51) and considering equation (49), the concentration of dispensed solids $C_o$ can be found to be given by equation (52), also $C_o$ can $$C_o = \frac{Q \cdot \rho_{dc}}{F + Q} \quad (52)$$

be verified independently.

Figure 10:
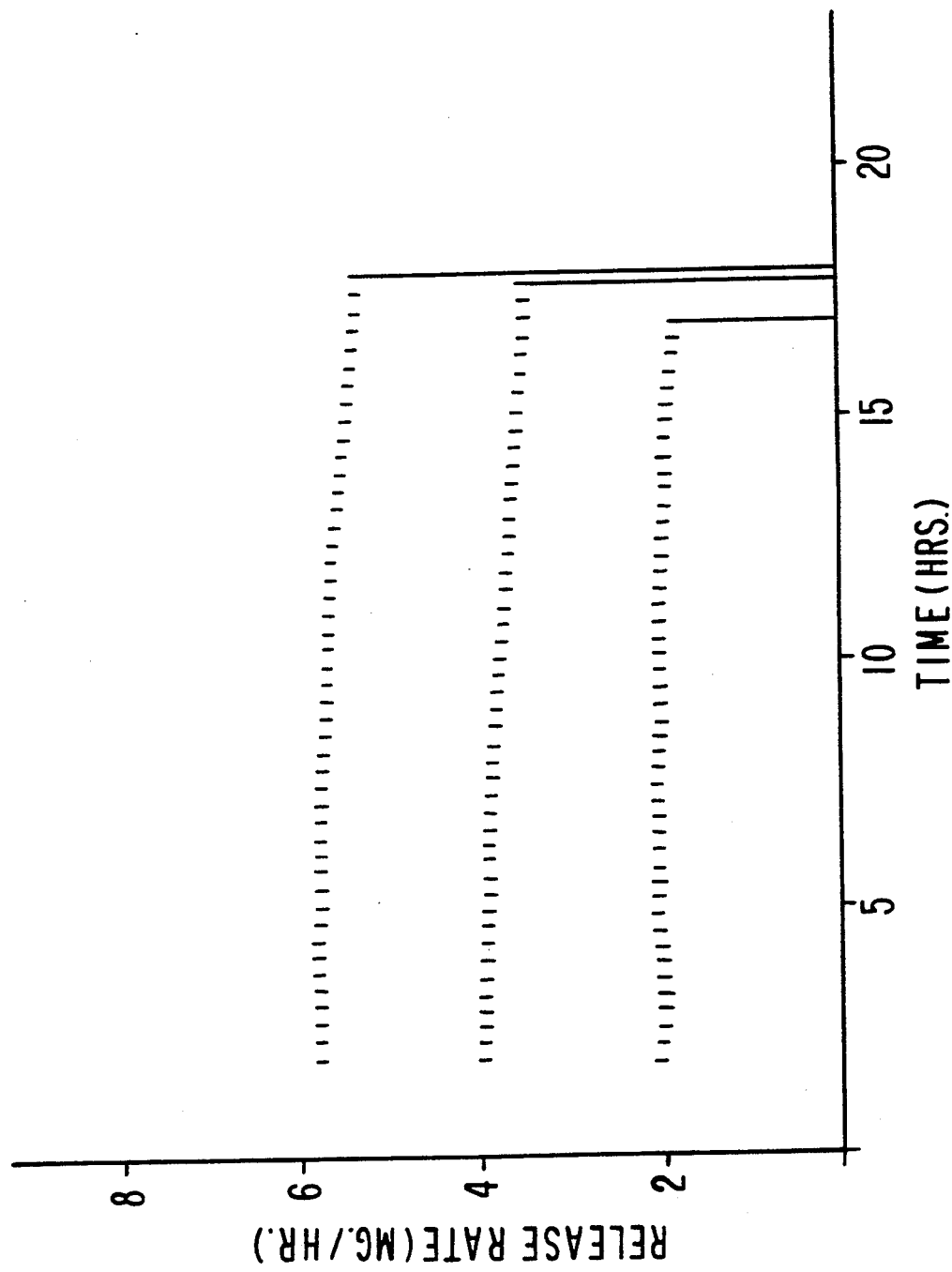
FIG. 10 depicts the release rate for three delivery systems, the top release rate pattern for a system comprising 99 mg of a drug, the middle line for a system comprising 66 mg of a drug, and the bottom line for a system comprising, 33 mg of a drug.

Based on the above description, three push-pull osmotic systems were designed to deliver a water soluble drug with parameters as listed in Table 2. The density of the push and drug compartment was respectively 1.4 and 1.2 gr/ml. The osmotic pressure in the drug compartment was 70 atm. The volume was allowed to swell 25 percent till hydration H=0.15, and the diameter and system area during that time decreased by about 15 percent. The release rate from these systems achieved a release rate as shown in FIG. 10 based on equations (48) and (50). The concentration of dispensed solids achieved a range of 500 to 900 mg/ml.

TABLE 2

| Design Parameters For Insoluble Drug | | | |
|---|---|---|---|
| Diameter (cm) | 0.79 | 1.03 | 1.19 |
| Drug content (mg) | 33 | 66 | 99 |
| Weight of drug layer (mg) | 165 | 330 | 495 |
| Weight of push layer (mg) | 82.5 | 165 | 247.5 |
| Membrane thickness (cm) | $12 \times 10^{-3}$ | $11 \times 10^{-3}$ | $9.9 \times 10^{-3}$ |
| Membrane | $6.35 \times 10^{-7}$ | $6.35 \times 10^{-7}$ | $6.35 \times 10^{-7}$ |

TABLE 2-continued

| Design Parameters For Insoluble Drug | | | |
|---|---|---|---|
| permeability (cm²/hr atm) | | | |
| Total system area A (cm²) | 1.9 | 3.1 | 4.1 |

EXAMPLE 2

An osmotic delivery device manufactured in the appearance of an osmotic tablet shaped, sized and adapted for oral admittance into the gastrointestinal tract is made as follows: a first osmotic drug composition is prepared by screening 355 g of poly(ethylene oxide), having an approximate molecular weight of 200,000, through a 40 mesh stainless steel screen, then 100 g of a calcium antagonist is passed through the 40 mesh screen, 25 g of hydroxypropylmethylcellulose is passed through the 40 mesh screen and, finally, 10 g of potassium chloride is passed through the 40 mesh screen. Next, all the screened ingredients are added to the bowl of a laboratory blender and the ingredients dry blended for 15 to 20 minutes to produce a homogeneous blend. Then, a granulation fluid is prepared comprising 250 ml of ethanol and 250 ml of isopropyl alcohol, and the granulating fluid added to the blending bowl; first, 50 ml is sprayed into the bowl with constant blending, then 350 ml of the granulation fluid is added slowly to the bowl and the wet mass blended for another 15 to 20 minutes. Then, the wet granules are passed through a 16 mesh screen and dried at room temperature for 24 hours. Next, 10 g of magnesium stearate is added to the dry granules, and the ingredients roll-mixed for 20 to 30 minutes on a standard two-roll mill.

Next, a second osmotic composition is prepared as follows: first, 170 g of poly(ethylene oxide) having a molecular weight of 5,000,000 is screened through a 40 mesh screen, then 72.5 g of sodium chloride is passed through the 40 mesh screen, and the ingredients added to a mixing bowl and blended for 10 to 15 minutes. Then, a granulation fluid is prepared by mixing 350 ml of methanol and 150 ml of isopropyl alcohol, and the granulation fluid added to the blending bowl in two steps. First, 50 ml of the granulation fluid is sprayed into the bowl with constant blending; then 350 ml of the granulation fluid is slowly added to the bowl and the wet blend mixed for 15 to 20 minutes to a homogeneous blend. Then, the wet blend is passed through a 16 mesh screen, spread on a stainless steel tray and dried at room temperature of 22.5° C. for 24 hours. The dried blend is passed through a 16 mesh screen, then roll milled with 5 g of magnesium stearate on a two-roll mill for 20 to 30 minutes.

A number of drug cores are prepared by pressing the two compositions on a Manesty Layerpress. The drug containing composition is fed into the cavity mold of the press and tamped into a solid layer. Then, the second osmotic composition is fed into the cavity overlaying the tamped layer and compressed into a solid layer to form a two-layered drug core.

Figure 11:
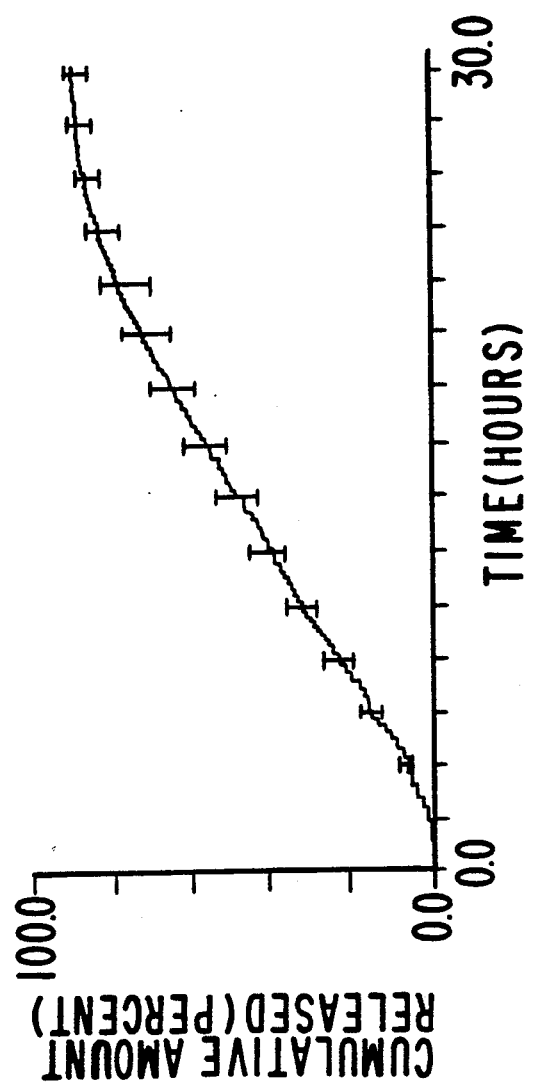
FIG. 11 depicts the cumulative amount of drug released from a device comprising two osmopolymer having two different molecular weights.

The drug cores next are coated with a semipermeable wall forming composition comprising 95 g of cellulose acetate having an acetyl content of 39.8% and 5 g of poly(ethylene glycol) 4000 in a solvent comprising 1960 ml of methylene chloride and 820 ml of methanol. The drug cores are coated with the semipermeable wall forming composition until the wall surrounds the drug core. A Wurster air suspension coater is used to form the semipermeable wall. The coated cores are then spread on a tray and the solvent evaporated in a circulating air oven at 50° C. for 65 hours. After cooling to room temperature, a 0.26 mm diameter passageway is laser drilled through the semipermeable wall connecting the exterior of the osmotic device with the composition containing the drug. The osmotic device weighed 262 mg and it contained 30 mg of drug in the first composition weighing 150 mg, the second composition weighed 75 mg and the semipermeable wall weighed 37 mg. The first composition of the osmotic device comprises 30 mg of the calcium antagonists, 106 mg of poly(ethylene oxide), 3 mg of potassium chloride, 7.5 mg of hydroxypropylmethylcellulose and 3 mg of magnesium stearate. The second osmotic composition comprises 51 mg of poly(ethylene oxide), 22 mg of sodium chloride and 1.5 mg of magnesium stearate. The device has a diameter of 8 mm, a surface area of 1.8 cm² and the semipermeable wall is 0.17 mm thick. The cumulative amount of drug released is depicted in FIG. 11.

EXAMPLE 3

Osmotic delivery systems are prepared having a first composition comprising 25 to 1000 mg of a calcium channel blocker 100 to 325 mg of poly(ethylene oxide) having a molecular weight of 200,000, 2 to 10 mg of potassium chloride, 5 to 30 mg of hydroxypropylmethylcellulose, and 2 to 10 mg of magnesium stearate; and a second composition comprising 30 to 275 mg of poly(ethylene oxide) having a molecular weight of 5,000,000, 20 to 75 mg of sodium chloride and 1 to 5 mg of magnesium stearate. The procedure of Example 1 is repeated for preparing osmotic devices having the following compositions: (a) an osmotic device having a first composition comprising 60 mg of the calcium channel blocker, 212 mg of poly(ethylene oxide), 6 mg of potassium chloride, 15 mg of hydroxypropylmethylcellulose and 6 mg of magnesium stearate; and a second composition comprising 102 mg of poly(ethylene oxide), 44 mg of sodium chloride, and 3 mg of magnesium stearate; and, (b) an osmotic device having a first composition comprising 90 mg of the calcium channel blocker, 318 mg of poly(ethylene oxide), 9 mg of potassium chloride, 22.5 mg of hydroxypropylmethylcellulose, and 146 mg of poly(ethylene oxide), 66 mg of sodium chloride, and 4.5 mg of magnesium stearate. In an embodiment, the osmotic device described in (a) and (b) further comprise a pulse coated layer of drug carried on the outer semipermeable wall. The pulse coat comprises 30 mg of the calcium channel blocker and hydroxypropylmethylcellulose. In operation in the fluid environment of use, the pulse coat provides instant drug availability for instant drug therapy.

EXAMPLE 4

An osmotic delivery system is prepared according to the procedure described above for administering a therapeutically effective amount of a member selected from the group consisting of nimodipine, nitrendipine, nisoldipine, nicardipine, felodipine, diltiazem, lidoflazine, tiapamil, gallopamil, amlodipine, and mioflazine.

EXAMPLE 5

An oral osmotic delivery device useful for the management of cardiovascular diseases is prepared according to the mode and manner of the invention. The device comprises a first composition, a drug composition, comprising 33 mg of a calcium antagonists, 122 mg of poly(ethylene oxide) having a molecular weight of 100,000, 8.25 mg of hydroxypropylmethylcellulose and 1.65 mg of magnesium stearate; and a second composition, a push composition, comprising 52.8 mg of poly(ethylene oxide) having a molecular weight of 5,000,000; 23.9 mg of sodium chloride, 4.13 mg of hydroxypropylmethylcellulose and 0.83 mg of magnesium stearate. The first and second composition are surrounded by a semipermeable wall comprising 95% cellulose acetate having an acetyl content of 39.8% and 5% poly(ethylene glycol) 4000. The osmotic device has at least one osmotic passageway 0.35 mm in diameter in the semipermeable wall connecting the drug composition with the exterior of the osmotic device. The device delivers 1.7 mg/hr of the drug over a prolonged period of 24 hours.

EXAMPLE 6

The procedure of Examples 2 to 4 is repeated for preparing osmotic devices containing from 5 mg to 150 mg of the drug. A series of osmotic devices are prepared containing 5 mg, 10 mg, 30 mg, 60 mg and 90 mg, up to 150 mg. These devices can comprise in the first composition from 50 mg to 750 mg of an osmopolymer and, optionally, 1 mg to 15 mg of an osmagent, and in the second composition from 20 mg to 320 mg of osmopolymer and 10 mg to 80 mg of osmagent. The devices have at least one osmotic passageway of 5 to 30 mils in diameter for delivering the drug. Individual devices can be prepared by following the procedures that have a rate of release of 0.25 mg, 0.5 mg, 0.6 mg, 0.8 mg, 1.3 mg, 2.7 mg and 3.0 mg per hour for 24 hours. The osmotic device is indicated for the management of plasma levels and it is indicated for treating cardiovascular conditions.

EXAMPLE 7

The procedures of the above examples are followed with all conditions as previously described except that the drug in the drug composition is an orally administered drug indicated for the management of cardiovascular diseases and it is a member selected from the group consisting of fendiline, diltiazem, perhexiline, and prenylamine.

EXAMPLE 8

An osmotic therapeutic device for the controlled and the continuous oral release of the beneficial calcium channel blocker drug verapamil is made as follows: 90 mg of verapamil, 50 mg of sodium carboxylvinyl polymer having a molecular weight of 200,000 and sold under the trademark Carbopol ® polymer, 3 mg of sodium chloride, 7.5 mg of hydroxypropylmethylcellulose and 3 mg of magnesium stearate are mixed thoroughly as described in Example 1, and pressed in a Manesty ® press with a 5/16 inch punch using a light pressure to produce a layer of the drug composition. Next, 51 mg of the carboxyvinyl polymer having a molecular weight of 3,000,000 and sold under the trademark Carbopol ® polymer, 22 mg of sodium chloride and 2 mg of magnesium stearate are blended thoroughly and added to the Manesty press, and pressed to form a layer of expandable, osmotic composition in contact with the layer of osmotic drug composition.

Next, a semipermeable wall is formed by blending 170 g of cellulose acetate, having an acetyl content of 39.8%, with 900 ml of methylene chloride and 400 ml of methanol, and spray coating the two layered compartment forming member in an air suspension machine until 5.1 mil thick semipermeable wall surrounds the compartment. The coated device is dried for 72 hours at 50° C. and then a 8 mil osmotic passageway is laser drilled through the semipermeable wall to connect the layer containing drug with the exterior of the device for releasing drug over a prolonged period of time.

EXAMPLE 9

An osmotic therapeutic drug delivery device is prepared by following the procedure of Example 6, with all manufacturing conditions as described heretofore, except that in the present example the drug composition comprises 90 mg of verapamil, 50 mg of sodium carboxyvinyl polymer having a molecular weight of 200,000, 7.5 mg of hydroxypropylmethylcellulose and 3 mg of magnesium stearate.

EXAMPLE 10

An osmotic, therapeutic device for the delivery of the drug ketoprofen for uses as an anti-inflammatory is prepared by first pressing in a Manesty press an osmotic drug composition containing 75 mg of ketoprofen, 300 mg of sorbitol, 30 mg of sodium bicarbonate, 26 mg of pectin, 10 mg of polyvinyl pyrrolidone, and 5 mg of stearic acid, and tamping the composition in a cavity to a single layer. Next, the cavity is charged with a second and greater force generating composition comprising 122 mg of pectin having a molecular weight of 90,000 to 130,000, 32 mg of mannitol, 20 mg of polyvinyl pyrrolidone, and 2 mg of magnesium stearate and pressed to form a second layer in contacting relation with the first layer. The second layer had a density of 1.28 g/cm$^3$ and a hardness score of greater than 12 kP. Next, the two layer core is surrounded with a semipermeable wall comprising 85 g of cellulose acetate having an acetyl content of 39.8%, and 15 g of polyethylene glycol 4000, 3 (wt/wt) percent solid in a wall forming solvent comprising 1960 ml of methylene chloride and 819 ml of methanol. The coated device is dried for 72 hours at 50° C., and then a 0.26 mm diameter passageway is laser drilled through the wall. The semipermeable wall is 0.1 mm thick, the device has an area of 3.3 cm$^2$, and it releases drug over a 12 hour period.

EXAMPLE 11

The procedure of Example 10 is followed for providing an osmotic device wherein the compartment contained a blend of osmopolymers. The compartment contained a first composition weighing 312 mg and consists of 48% ketoprofen drug, 38% poly(ethylene oxide) osmopolymer having a molecular weight of 200,000, 10% poly (ethylene glycol) osmopolymer having a molecular weight of 20,000, 2% sodium chloride and 2% magnesium stearate; and a second composition weighing 150 mg and consisting of 93% poly(ethylene oxide) having a molecular weight of 5,000,000, 5% sodium chloride and 2% magnesium stearate.

EXAMPLE 12

In this example, the increase in osmotic pressure for a number of compositions comprising an osmagent and an osmopolymer are measured for demonstrating the operative advantage provided by the invention. The measurements are made by measuring the amount of water imbibed across the semipermeable wall of a bag containing an osmagent, or an osmopolymer, or a composition comprising an osmagent and an osmopolymer. The semipermeable wall of the bag is formed of cellulose acetate having an acetyl content of 39.8%. The measurements are made by weighing the dry ingredients of the semipermeable bag, followed by weighing the blotted semipermeable bag, after the bag is in a water bath at 37° C. for various lengths of time. The increase in weight is due to water imbibition across the semipermeable wall caused by the osmotic pressure gradient across the wall. The osmotic pressure curves are illustrated in FIG. 10. In FIG. 11 the curved line with the triangles represents the osmotic pressure for poly(ethylene oxide) having a molecular weight of 5,000,000; the curved line with the circles represents the osmotic pressure for a composition comprising poly(ethylene oxide) having a molecular weight of 5,000,000 and sodium chloride with the ingredients present in the composition in the ratio of 9.5 parts osmopolymer to 0.5 parts osmagent; the curved line with squares represents a composition comprising the same osmopolymer and osmagent in the ratio of 9 parts osmopolymer to one part osmagent; the curved lines with hexagon represents the same composition comprising the osmopolymer an osmagent in the ratio of 8 parts to 2 parts; and, the dashed lines represent the osmagent sodium chloride. The mathematical calculations are made using the formula $dw/dt = K\Delta\pi A/h$, wherein $dw/dt$ is the rate of water imbibition over time, $A$ is the area of the semipermeable wall, and $K$ is the permeability coefficient. Also, in FIG. 12, $W_H/W_p$ is the amount of water imbibed divided by the dry weight of osmopolymer plus osmagent.

EXAMPLE 13

An osmotic therapeutic device for dispensing naproxen is prepared by screening through a 40 mesh screen a composition comprising 49% of naproxen, 46% poly(ethylene oxide) having a molecular weight of 100,000, and 3% hydroxypropylmethylcellulose, and then blending the screened composition with an alcohol solvent used in the ratio of 75 ml of solvent to 100 g of granulation. The wet granulation is screened through a 16 mesh screen, dried at room temperature for 48 hours under vacuum, and blended with 2% magnesium stearate that has been passed through an 80 mesh screen. The composition is compressed as described above.

Next, a composition comprising 73.9% of pectin having a molecular weight of 90,000 to 130,000, 5.8% microcrystalline cellulose, 5.8% polyvinyl pyrrolidone, 14.3% sodium chloride and 2% sucrose is passed through a 40 mesh screen, blended with an organic solvent in the ratio of 100 ml of solvent to 100 g of granulation for 25 minutes, passed through a 16 mesh screen, dried for 48 hours at room temperature under vacuum, again passed through a 16 mesh screen, blended with 2% magnesium stearate and then compressed onto the compressed layer described in the above paragraph. The dual layered drug core is coated by dipping in a wall forming composition comprising 80% cellulose acetate having an acetyl content of 39.8%, 10% polyethylene glycol 3350, and 10% hydroxypropylmethylcellulose. An osmotic passageway is drilled through the wall communicating with the drug containing composition. The osmotic diameter is 0.38 mm.

EXAMPLE 14

The procedure of Example 11 is repeated with all conditions as described, except that the osmopolymer in the drug composition is polyoxyethylene polyoxypropylene block copolymer having a molecular weight of about 12,500.

EXAMPLE 15

Figure 13:
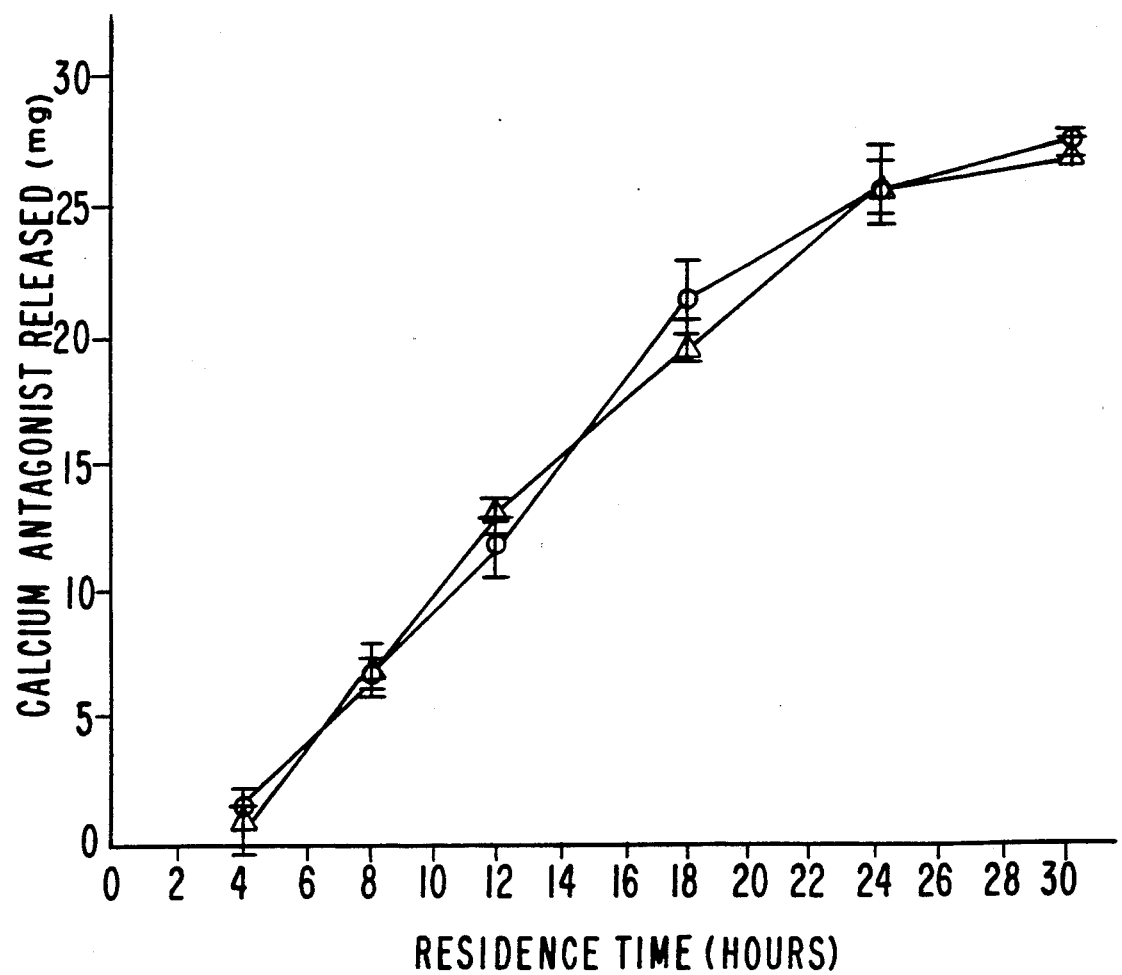
FIG. 13 illustrates the in vivo and in vitro cumulatie release for a drug delivered by an osmotic device.

The in vivo and in vitro mean cumulative release of a calcium antagonist from an osmotic device comprising a composition adjacent to the passageway comprising 30 mg of the drug, 106.5 mg of poly(ethylene oxide) having a molecular weight of 200,000, 3 mg of potassium chloride, 7.5 mg of hydroxypropylmethylcellulose, and 3 mg of magnesium stearate; a composition distant from the passageway comprising 52 mg of poly(ethylene oxide) having a molecular weight of 5,000,000, 22 mg of sodium chloride and 1.5 mg of magnesium stearate; and a semipermeable wall comprising 95% cellulose acetate having an acetyl content of 39.8% and 5% hydroxypropylmethylcellulose is measured in vivo in laboratory dogs and in vitro in the laboratory. The amounts of drug released at various times in vivo were determined by administering a series of devices to the animals and measuring the amount released from the corresponding device at the appropriate residence time. The results are depicted in FIG. 13. In FIG. 13 the circles represent the in vivo cumulative release and the triangles represent the in vitro mean cumulative release.

EXAMPLE 16

The procedure of Example 12 is followed for making an osmotic therapeutic delivery system comprising: a first drug composition weighing 638 mg and consisting of 96% cephalexin hydrochloride, 2% granular core starch and 2% magnesium stearate; a second, or osmotic driving composition weighing 200 mg and consisting of 68.5% poly(ethylene oxide) having a molecular weight of 5,000,000, 29.5% sodium chloride, and 2% magnesium stearate; a semipermeable wall weighing 55.8 mg consisting of 80% cellulose acetate having an acetyl content of 39.8%, 10% polyethylene glycol 4000, and 10% hydroxypropyl methylcellulose; and an osmotic orifice having a diameter of 0.39 mm. The device has an average rate of release of about 54 mg per hour over a period of 9 hours.

EXAMPLE 17

The procedures described above are followed in this example for manufacturing an osmotic device for delivering the antipsychotic drug haloperidol to the gastrointestinal tract of a human. The osmotic delivery system comprises a first or drug composition comprising 11 mg of haloperidol, 245 mg of poly(ethylene oxide) having a molecular weight of about 100,000, 13.8 mg of hydroxypropylmethylcellulose and 5.5 mg of magnesium stearate; and, a second composition, initially in laminar arrangement with the first composition, which second composition consists essentially of 122 mg of poly(ethylene oxide) having a molecular weight of about 5,000,000, 56 mg of sodium chloride, 10 mg of hydroxypropylmethyl cellulose and 0.95 mg of magnesium stearate. The two compositions are surrounded by a semipermeable wall comprising 22.5 mg of cellulose acetate having an acetyl content of 39.8% and 2.5 mg of poly(ethylene glycol) 3350. The device has an osmotic passageway of 0.36 mm. The device delivers about 0.8 mg per hour over a 14 hours time period.

EXAMPLE 18

The procedure of Example 17 is repeated for preparing a series of osmotic devices housing a drug composition containing from 1 mg to 125 mg of haloperidol for dispensing a dosage of 0.1 mg, 1 mg, 2 mg, or 10 mg per hour over a prolonged period of at least 12 hours, or a cumulative dosage of 0.01 mg/kg/day to 0.075 mg/kg/day. The osmotic devices can be administered once, twice or thrice a day.

EXAMPLE 19

The procedure set forth above is repeated for providing an osmotic device for dispensing the nonsteroidal, anti-inflammatory, antipyretic, analgesic drug ibuprofen. The oral osmotic device comprises a first lamina composition consisting of 198 mg of ibuprofen and a second lamina composition consisting of 132 mg of poly(ethylene oxide) having a molecular weight of 5,000,000. The laminae compositions are surrounded by a semipermeable wall consisting essentially of 48.1 mg of cellulose acetate having an acetyl content 32%. The device has an osmotic passageway connecting the first lamina composition with the exterior of the device. The device has an average rate of release of 12.7 mg per hour over a 12 hour dispensing period. Similar osmotic devices are prepared containing 50 mg, 150 mg, 200 mg, 300 mg, 400 mg, 500 mg, and 600 mg for the anti-inflammatory, analgesic and antipyretic activities.

EXAMPLE 20

The procedures described above are followed for providing an osmotic device housing the non-steroidal drug, with anti-inflammatory, antipyretic and analgesic properties, indomethacin. The compartment of the device houses a first layer comprising 50 mg of indomethacin, 8.3 mg of hydroxypropyl methyl cellulose, 3.3 mg of magnesium stearate and 105 mg of poly(ethylene oxide) having a molecular weight of 100,000; and a second layer consisting of 52.5 mg of poly(ethylene oxide) having a molecular weight of 5,000,000, 24.2 mg of sodium chloride, 4.2 mg of hydroxypropylmethylcellulose and 1.67 mg of magnesium stearate. The device has a semipermeable wall comprising 95% (19.0 mg) cellulose acetate having an acetyl content of 39.8%, and 5% (1 mg) poly(ethylene glycol) 4000. The device has an osmotic passageway of 0.36 mm diameter for release of indomethacin. The device delivers 93% of the indomethacin over 18 hours. Similar devices are provided housing 25 mg and 75 mg of indomethacin for administering b.i.d. or t.i.d. for establishing steady-state plasma levels.

EXAMPLE 21

The procedures described above are followed for providing an osmotic device comprising a drug layer of 80 mg of isosorbide di-nitrate, 80 mg of lactose, 208 mg of poly(ethylene oxide) having a molecular weight of 200,000, 19.5 mg of hydroxypropylmethylcellullose and 3.9 mg of magnesium stearate, and a second expandable layer of 239 mg of poly(ethylene oxide) having a molecular weight of 5,000,000, 13 mg of hydroxypropylmethylcellulose, and 5.2 mg of magnesium stearate. The device has a semipermeable wall comprising 80% (36 mg) cellulose acetate having an acetyl content of 39.8%, 10% (4.5 mg) poly(ethylene glycol) 4000, and 10% (4.5 mg) hydroxypropylmethyl cellulose. The device has an osmotic passageway with a diameter of 0.51 mm and is clinically indicated for the relaxation of smooth muscle and treating angina pectoris.

EXAMPLE 22

The procedures described above are followed for making an osmotic device comprising a drug layer of 250 mg of alpha-methyldopa, levo-3-(3,4-dihydroxyphenyl)-2-methylalamine, 97.2 mg of poly(ethylene oxide) having a molecular weight of 200,000, 18.5 mg of hydroxypropyl methylcellulose and 8.7 mg of magnesium stearate, and a second layer of 226.6 mg of poly(ethylene oxide) having a molecular weight of 5,000,000, 12.3 mg of hydroxypropylmethylcellulose, and 4.9 mg of magnesium stearate. The device has a semipermeable wall comprising 65 weight percent (wt %), (15.5 mg), of cellulose acetate having an acetyl content of 39.8%, 17.5 wt % (4.2 mg), poly(ethylene glycol) 3350, and 17.5 wt % (4.2 mg) of hydroxypropylmethylcellulose. The device has an osmotic passageway of 0.51 mm communicating with the drug lamina for dispensing the drug from the device. The drug is indicated as an antihypertensive possessing decarboxylose inhibitor action in animals and in man. Similar devices can be prepared housing 125 mg to 500 mg of the drug.

EXAMPLE 23

The procedures described above are followed for providing an osmotic device comprising a first drug layer comprising 50 mg of hydrochlorothiazide, 189 mg of poly(ethylene oxide) having a molecular weight of 200,000, 1.0 mg of hydroxypropylmethylcellulose, and 2.5 mg of magnesium stearate; and a second expandable push layer comprising 280 mg of poly(ethylene oxide) having a molecular weight of 5,000,000, 15.4 mg of hydroxypropylmethylcellulose, and 0.2 mg of magnesium stearate. The device has a semipermeable wall comprising 95 wt % (54.4 mg) of cellulose acetate having an acetyl content of 39.8% and 5 wt % (2.9 mg) of poly(ethylene glycol) 3350. The device has an osmotic passageway with a diameter of 0.51 mm in the semipermeable wall communicating with the drug. Clinically, hydrochlorothiazide is a diuretic-antihypertensive. The osmotic device can contain from 12.5 to 250 mg given in 1 to 3 doses daily.

EXAMPLE 24

The procedures described above are followed for providing an osmotic device comprising a first drug layer comprising of 6 mg of an alpha adrenoreceptor blocker, 135 mg of poly(ethylene oxide) having a molecular weight of 100,000, 7.5 mg of hydroxypropylmethylcellulose, and 3.0 mg of magnesium stearate; and an expandable push layer initially in close contacting arrangement comprising 47.3 mg of poly(ethylene oxide) having a molecular weight of 5,000,000, 21.8 mg of sodium chloride, 3.8 mg of hydroxypropylmethylcellulose, and 1.5 mg of magnesium stearate. The device has a semipermeable wall comprising 95 wt % (25 mg) of cellulose acetate having an acetyl content of 39.8%, and 5 wt % (1.32 mg) of poly(ethylene glycol) 4000. The device has an osmotic passageway of 0.37 mm. The device, after a start-up of about 1 hour, delivers about 0.24 mg per hour over a period of 26 hours. Devices containing from 1 mg to 125 mg of drug can be prepared for their vasodilator effect as related to blockade of postsynaptic alpha-adrenoceptors. The device also can be used for the treatment of hypertension.

EXAMPLE 25

The procedure of Example 24 repeated for providing osmotic devices containing in the first layer from 1 mg to 15 mg of a blocking alpha adrenoreceptor from 25 mg to 375 mg of osmopolymer and, optionally, from 0.5 mg to 7.5 mg of osmagents and a second layer comprising 15 mg to 250 mg of osmopolymer and, optionally, from 10 mg to 75 mg of osmagent.

EXAMPLE 26

The procedure of Example 24 Is followed for providing an osmotic device comprising: a first layer composition weighing 150.70 mg comprising 4 wt % of a blocking alpha-adrenoreceptor drug, 89 wt % Polyox® N-10 poly(ethylene oxide) having a molecular weight of 100,000, 5 wt % hydroxypropylmethylcellulose, and 2 wt % magnesium stearate; a second layer composition weighing 150.70 mg comprising 92 wt % Polyox® Coagulant poly(ethylene oxide) having a molecular weight of 5,000,000, 5 wt % hydroxypropylmethylcellulose, 1 wt % ferric oxide, and 2 wt % magnesium stearate. The osmotic device semipermeable wall weighed 23.70 mg comprising 95 wt % cellulose acetate having an acetyl content of 39.8% and 5 wt % poly(ethylene glycol) 4000. The osmotic passageway has a diameter of 0.370 mm connecting the exterior of the device with the drug layer.

EXAMPLES 27-28

The procedures described above are repeated with all procedures as previously described, except that the osmotic device contained an alpha-adrenergic blocking drug selected from the the group consisting of trimazosin, phenoxybenzamine hydrochloride and phentolamine hydrochloride.

EXAMPLES 29-30

The procedures described above are repeated with all procedures as described, except that in the present devices the first composition in the compartment contained from 1 mg to 125 mg of a member selected from the group consisting essentially of anhydrous theophylline, salbutamol base, diazepam and furosemide.

EXAMPLES 31-34

The procedures for manufacturing an osmotic device for dispensing an angiotensin converting enzyme drug through at least one pore in a cellulose acylate wall of the device is manufactured as describe herein with the angiotensin converting enzyme inhibitor a member selected from the group consisting of lisinopril, enalapril, captopril, ramipril and enalapriat.

EXAMPLES 35-40

The procedures for manufacturing an osmotic device for administering a gastrointestinal histamine receptor antagonists in a therapeutically effective amount for treating ulcers through at least one pore-passageway of a cellulosic wall is followed with the manufacture as set forth with the drug selected from the group consisting of famotidine, cimetidine, ranitidine, nizatidine and etintidine, from 100 mg to 450 mg every 12 to 24 hours one to three times daily.

EXAMPLE 41

A dosage form for administering the beneficial, gastrointestinal administrable drug, salbutamol hydrochloride, is made according to the above procedures. The wall in the present example is applied in an air suspension machine and it comprises a microporous wallforming composition. The microporous composition comprises 45% by weight of cellulose acetate having an acetyl content of 39.8%, 45% by weight of sorbitol, and 10% by weight of polyethylene glycol 400. In operation, in the fluid environment of the gastrointestinal tract, the sorbitol is leached from the wall providing thereby a plurality of microporous passageways of controlled porosity for release of the drug salbutamol hydrochloride from the dosage forms.

EXAMPLE 42

A dosage form for administering the beneficial gastrointestinal administrable drug, theophylline isopropanolamine is made according to the above procedures. The wall in the present example is applied in an air suspension machine and it comprises a microporous wallforming composition. The microporous composition comprises 55% by weight of cellulose acetate having an acetyl content of 39.8%, 40% by weight of sorbitol and 5% by weight of polyethylene glycol 400. In operation, in the fluid environment of the gastrointestinal tract, the sorbitol is leached from the wall providing a plurality of micropores. The micropores of controlled porosity provide fluid access through the wall to the osmopolymers. The osmopolymers act in concert to deliver the drug through a preformed passageway in the wall to the drug formulation.

The novel osmotic system of this invention uses dual means for the attainment of precise release rate of drugs that are difficult to deliver in the environment of use, while simultaneously maintaining the integrity and the character of the system. While there has been described and pointed out features and advantages of the invention as applied to the presently preferred embodiments, those skilled in the dispensing art will appreciate that various modifications, changes, additions, and omissions in the system illustrated and described can be made without departing from the spirit of the invention.

We claim:

1. An improvement in a device for delivering a beneficial agent composition to a fluid environment of use, wherein the device comprises:
   (a) a wall comprising a composition that is permeable to the passage of fluid and is substantially impermeable to the passage of agent, which wall surrounds and forms;
   (b) a compartment, and wherein the improvement comprises;
   (c) a beneficial agent composition comprising a beneficial agent and 10% to 90% of an osmopolymer in the compartment, which beneficial agent composition is delivered substantially as a ribbon, at a rate expressed by $$\frac{dm}{dt} = \left(\frac{dV}{dt}\right)_t \cdot C_D \text{ wherein } \frac{dm}{dt}$$

is the does of beneficial agent delivered in unit time, $$\left(\frac{dV}{dt}\right)_t$$

is the total volume of the agent composition delivered in unit time, and $C_D$ is the amount of beneficial agent mixed with the osmopolymer composition delivered from the device;

(d) a push composition in contact with the beneficial agent composition in the compartment, which push composition, in the presence of fluid that enters the device, increases in dimension and pushes the beneficial agent composition from the device; and, (e) exit means in the wall for delivering the beneficial agent composition from the device, at a controlled rate over time.

2. An improvement in a device for delivering a beneficial agent to a fluid environment of use, wherein the device comprises:

(a) a wall comprising a composition that is permeable to the passage of fluid and is substantially impermeable to the passage of agent, which wall surrounds and defines;

(b) a compartment, and wherein the improvement comprises;

(c) a beneficial agent composition in the compartment comprising 10% to 90% of an osmopolymer and an osmagent that exhibit fluid influx, which beneficial agent composition is delivered substantially as a ribbon, and when the device is in operation in a fluid environment, a fluid influx $$F=\left(\frac{dV}{dt}\right)_D,$$

wherein dV is the volume influxed in unit time dt;

(d) a push composition in contact with the beneficial agent composition in the compartment, said push composition exhibiting, when the device is in operation, a fluid influx $$Q=\left(\frac{dV}{dt}\right)_p$$

wherein dV is the volume influxed in unit time dt; and, (e) at least one exit orifice in the wall for delivering the beneficial agent by the cooperating operation of beneficial agent composition and the push composition acting together for delivering the beneficial agent through said orifice.

3. An improvement in a device for delivering a beneficial agent to a fluid environment of use, wherein the device comprises:

(a) a wall comprising a composition that is permeable to the passage of fluid and is substantially impermeable to the passage of agent, which wall surrounds;

(b) a compartment, and wherein the improvement comprises:

(c) a beneficial agent composition in the compartment that is delivered substantially as a ribbon, which composition comprises 10% to 90% of means for absorbing fluid that enters the compartment at a rate $$F=\left(\frac{dV}{dt}\right)_A$$

for providing at least a fraction of the composition comprising fluid in unit time dt;

(d) a push composition in contact with the beneficial agent composition in the compartment, which push composition absorbs fluid that enters the compartment at a rate $$Q=\left(\frac{dV}{dt}\right)_p$$

for providing at least in part a fraction of the push needed for pushing the beneficial agent compoition from the device at a rate comprising $$\frac{dm}{dt}=\left(\frac{dV}{dt}\right)_p\cdot F_D\cdot \rho_{dc}$$

wherein $F_D$ is the fraction of beneficial agent in the agent composition and $\rho_{dc}$ is the density of the beneficial agent composition; and, (e) at least one exit pore passageway in the wall for delivering the beneficial agent composition from the device, at a rate governed by the wall, the beneficial agent composition and the push composition interacting to deliver the beneficial agent through the orifice.

* * * * *

UNITED STATES PATENT AND TRADEMARK OFFICE
CERTIFICATE OF CORRECTION

PATENT NO. : 5,082,668
DATED : January 21, 1992
INVENTOR(S) : Patrick S.L. Wong, Brian L. Barclay, Joseph C. Deters, Felix Theeuwes It is certified that error appears in the above-indentified patent and that said Letters Patent is hereby corrected as shown below:

Title page, in field [*], please add "Notice: The portion of the term of this patent subsequent to September 16, 2003, has been disclaimed."

Signed and Sealed this

Twenty-fourth Day of December, 1996

Attest:

BRUCE LEHMAN

*Attesting Officer*   *Commissioner of Patents and Trademarks*